US008729256B2

(12) United States Patent
Moliner-Marin et al.

(10) Patent No.: US 8,729,256 B2
(45) Date of Patent: May 20, 2014

(54) ISOMERIZATION OF SUGARS

(75) Inventors: Manuel Moliner-Marin, Valencia (ES); Yuriy Roman-Leshkov, Somerville, MA (US); Mark E. Davis, Pasadena, CA (US); Eranda Nikolla, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 247 days.

(21) Appl. No.: 13/007,389

(22) Filed: Jan. 14, 2011

(65) Prior Publication Data

US 2011/0207923 A1  Aug. 25, 2011

Related U.S. Application Data

(60) Provisional application No. 61/295,637, filed on Jan. 15, 2010, provisional application No. 61/305,480, filed on Feb. 17, 2010, provisional application No. 61/359,782, filed on Jun. 29, 2010, provisional application No. 61/421,840, filed on Dec. 10, 2010.

(51) Int. Cl.

| C07H 1/00 | (2006.01) |
|---|---|
| C07H 3/00 | (2006.01) |
| C08B 37/00 | (2006.01) |
| C07H 3/02 | (2006.01) |

(52) U.S. Cl.
USPC ...................................................... 536/125

(58) Field of Classification Search
None
See application file for complete search history.

(56) References Cited

U.S. PATENT DOCUMENTS

| 4,373,025 | A | 2/1983 | Neuzil et al. |
| 4,410,501 | A | 10/1983 | Taramasso et al. |
| 7,572,925 | B2 | 8/2009 | Dumesic et al. |
| 2004/0121437 | A1 | 6/2004 | Scheels |
| 2005/0201920 | A1 | 9/2005 | Shan et al. |
| 2010/0121096 | A1 | 5/2010 | Taarning et al. |

FOREIGN PATENT DOCUMENTS

| EP | 0176621 | 4/1986 |
| EP | 0302970 | 2/1989 |
| JP | 2001-114511 | 4/2001 |
| WO | WO 2007146636 A1 * | 12/2007 |

OTHER PUBLICATIONS

Moliner et al. PNAS, vol. 107, No. 14, Apr. 6, 2010, pp. 6164-6168.*
Lima et al. Applied Catalysis A: General 339 (2008) 21-27.*
Corma et al. ARKIVOC 2007 (viii) 40-48.*
PTC tips, PTO Reaction of the Month, http://www.phasetransfer.com/03tip9.htm, 2003.*
Andy and David, "Dehydrogenation of Propane Over Platinum Containing CIT-6", Ind. Eng. Chem. Res., Jun. 2004, 43(12), 2922-2928.
Baerlocher et al., "Atlas of Zeolite Framework Types", Fourth Edition, 1996, 62-63.
Bermejo-Deval et al., "Framework and Extraframework Tin Sites in Zeolite Beta React Glucose Differently", ACS Catalysis, Oct. 23, 2012, 9 pages.
Blasco et al., "Synthesis, Characterization, Catalytic Activity of Ti-MCM-41 Structures", J. Catal., Sep. 1995, 156(1), 65-74.
Corma et al., "Al-Free Sn-Beta Zeolite as a Catalyst for the Selective Reduction of Carbonyl Compounds (Meerwein-Ponndorf-Verley Reaction)", J. Am. Chem. Soc, Apr. 3, 2002, 124(13), 3194-3195.
Corma et al., "Lewis Acidic Sn(IV) Centers—Grafted Onto MCM-41—as Catalytic Sites for the Baeyer—Villiger Oxidation With Hydrogen Peroxide", Journal of Catalysis., Oct. 2003, 219(1), 242-246.
Corma et al., "Mesoporous Molecular Sieve Sn-MCM-41 as Baeyer-Villiger Oxidation Catalyst for Sterically Demanding Aromatic and α,β-unsaturated Aldehydes", Arkivoc, Mar. 2005, 124-132.
Corma et al., "Sn-Zeolite Beta as a Heterogeneous Chemoselective Catalyst for Baeyer-Villiger Oxidations", Nature, Jul. 26, 2001, 412(6845), 423-425.
Corma et al., "Water Resistant, Catalytically Active Nb and Ta Isolated Lewis Acid Sites, Homogeneously Distributed by Direct Synthesis in a Beta Zeolite", J. Phys. Chem. C., Jun. 2009, 113(26), 11306-11315.
Corma et al., "Lewis acids: From conventional homogeneous to green homogenous and heterogeneous catalysis", Chem. Rev., 2003, 103(11), 4307-4365.
Davis et al., "Aqueos-Phase Monosaccharide and Disaccharide Isomerization and Epimerization over Lewis Acid Sites in Hydrophobic Molecular Sieves", Elseveir Editorial System for Journal of Catalysis, 2013, 102 pages.
Gounder et al., "Beyond Shape selective catalysis with zeolites: Hydrophobic void spaces in zeolites enable catalysis in liquid water", AICHE Journal, Jan. 24, 2013, 40 pages.
Hayashi and Sasaki, "Tin-Catalyzed Conversion of Trioses to Alkyl Lactates in Alcohol Solution", Chem. Commun., Apr. 2005, 21, 2716-2718.
Holm et al., "Conversion of Sugars to Lactic Acid Derivatives Using Heterogeneous Zeotype Catalysts", Apr. 30, 2010, 328, 602-605.
International Patent Application No. PCT/US2011/021301: Written opinion dated May 30, 2012, 4 pages.
Khouw et al., "Synthesis and Physicochemical Properties of Zeolites Containing Framework Titanium", Micropor. Mater, 2, Jan. 1994, 425-437.
Lee et al, "Effective Gene Silencing by Multilayered siRNA-Coated Gold Nanoparticles", Small, 2011, 7, 3, 364-370.
Lytton-Jean et al., "Five Years of siRNA Delivery: Spotlight on Gold Nanoparticles", Small, 2011, 7, 14, 1932-1937.
Roman-Leshkov et al., "Mechanism of Glucose Isomerization Using a Solid Lewis Acid Catalyst in Water", Angew. Chem. Intl, ed., Oct. 2010, 49, 8954-8957.
Roman-Leshkov et al., "Supporting Information—Supplementary Material", Angewandte Chemie, Nov. 2010, 8 pages.
Taarning et al., "Zeolite-Catalyzed Isomerization of Triose Sugars", Chem. Sus. Chem, Jun. 2009, 2(7), 625-627.
Tewari, "Supplementary Information—Thermodynamic Data", Applied Biochemistry and Biotechnology, Dec. 1990, 23(3), 187-203.

* cited by examiner

*Primary Examiner* — Layla Bland
(74) *Attorney, Agent, or Firm* — Baker & Hostetler LLP

(57) ABSTRACT

Disclosed are processes for isomerizing saccharides. Also disclosed are processes for converting saccharides to furan derivatives. Also disclosed are processes for converting starch to furan derivatives.

70 Claims, 35 Drawing Sheets

TS-1
(5.5-6 Å)

Ti-Beta, Sn-Beta
(7.5-8 Å)

Ti-MCM-41, Sn-MCM-41
(35 Å)

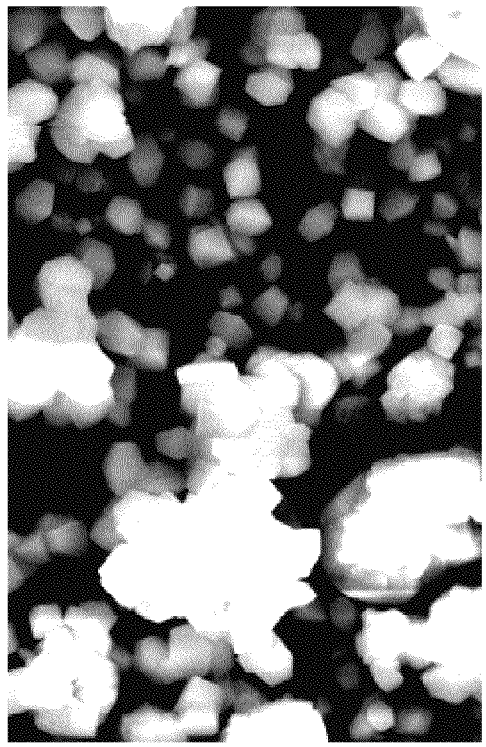
50μm  *FIG. 8*
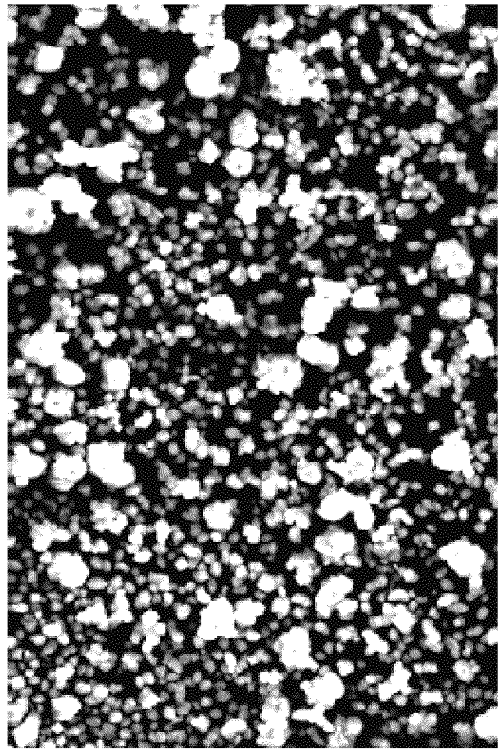
200μm  *FIG. 9*
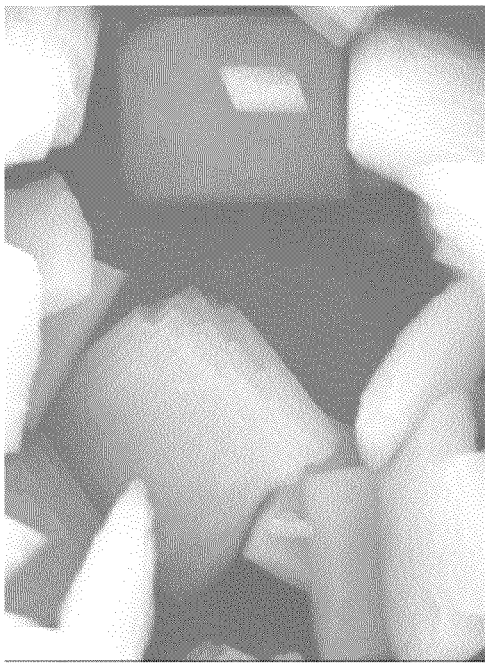
3μm  *FIG. 10*
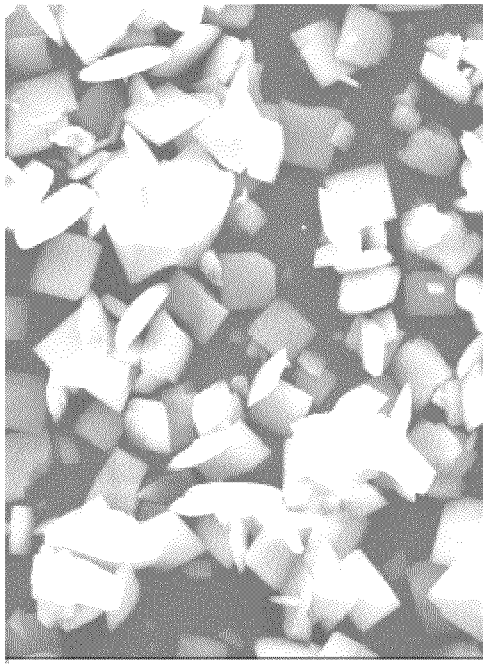
20μm  *FIG. 11*

Mag = 2.80 KX    10μm    EHT = 10.00kV
                         WD = 13 mm

Mag = 2.86 KX    10μm    EHT = 10.00kV
                         WD = 13 mm

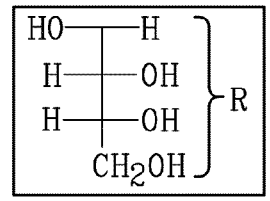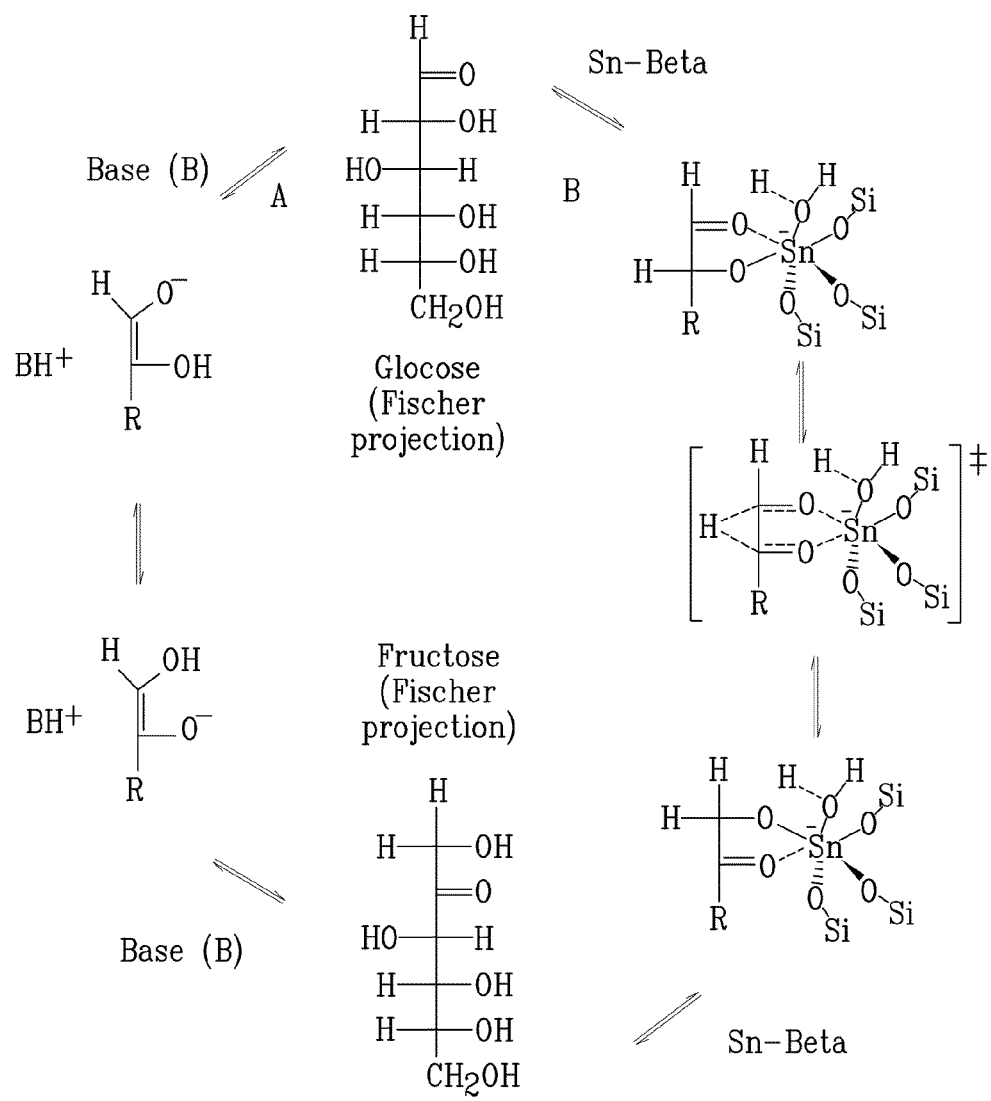
FIG. 18

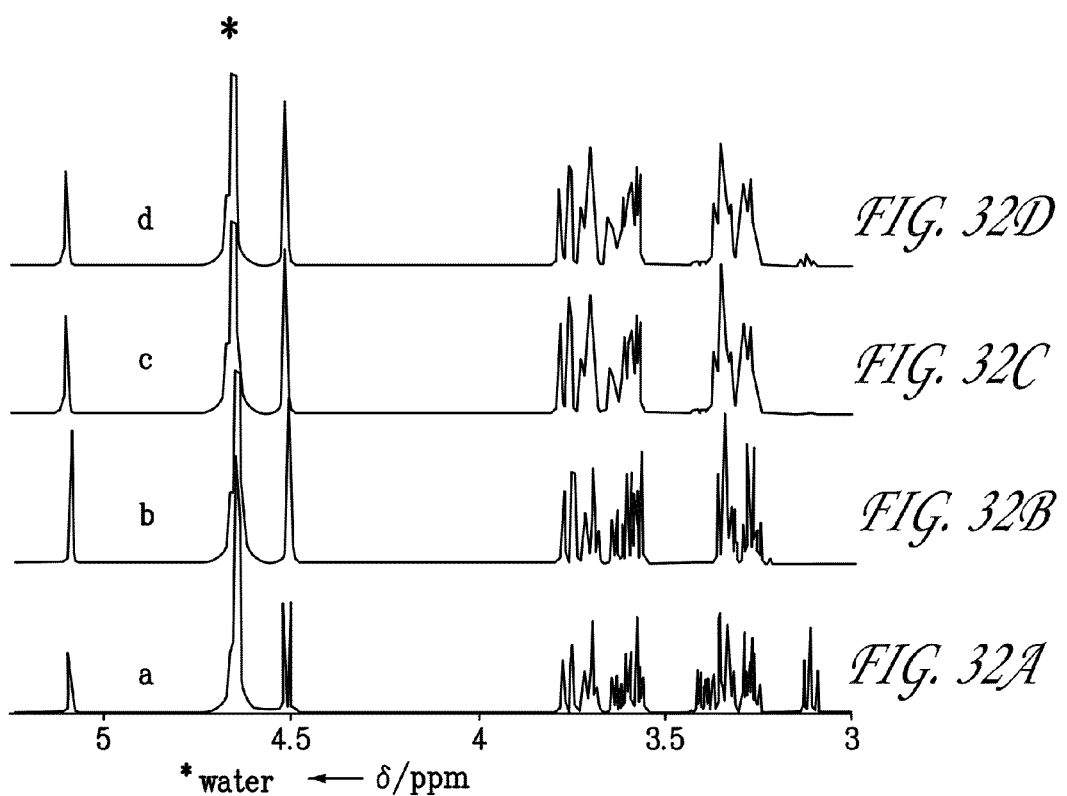
FIG. 32D
FIG. 32C
FIG. 32B
FIG. 32A
*water ← δ/ppm
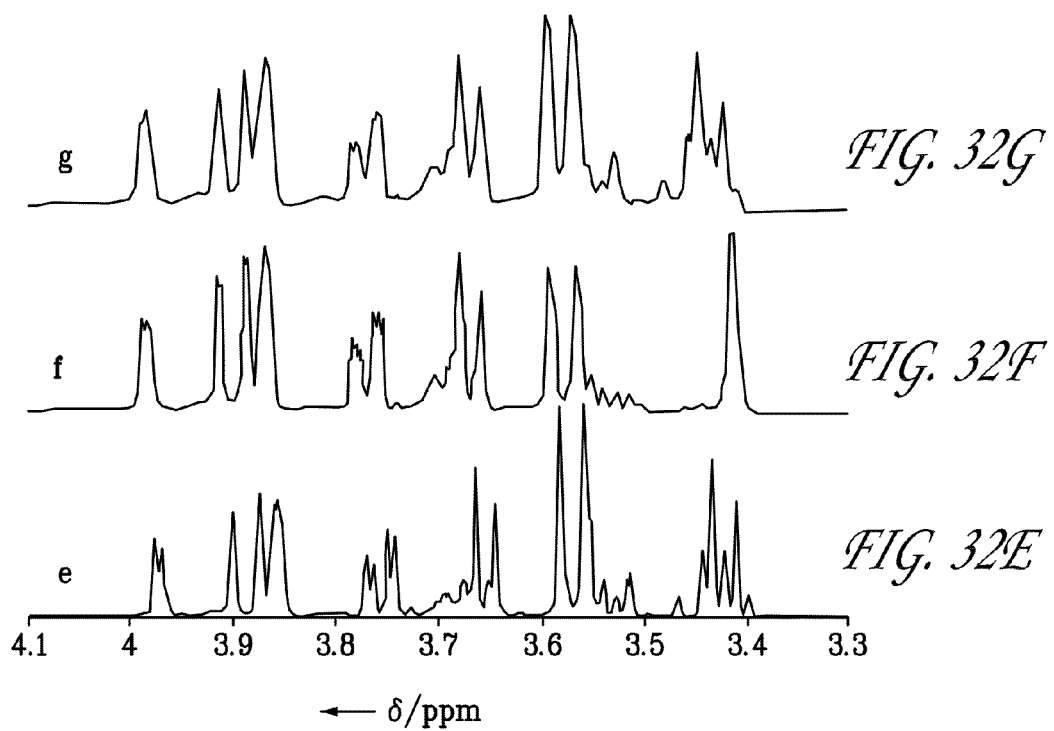
FIG. 32G
FIG. 32F
FIG. 32E
← δ/ppm

ISOMERIZATION OF SUGARS

CROSS REFERENCE TO RELATED APPLICATIONS

This application claims priority under 35 U.S.C. §119(e) to U.S. Provisional Application No. 61/295,637, filed on Jan. 15, 2010, entitled Catalysts for the Isomerization of Sugars, U.S. Provisional Application No. 61/305,480, filed on Feb. 17, 2010, entitled Catalysts for the Isomerization of Sugars, U.S. Provisional Application No. 61/359,782, filed on Jun. 29, 2010, entitled New Catalysts for the Isomerization of Sugars, and U.S. Provisional Application No. 61/421,840, filed on Dec. 10, 2010, entitled New Catalysts for the Isomerization of Sugars, each of which are incorporated herein by reference in their entirety.

The subject matter disclosed herein was made with government support under grant number DE-SC0001004 awarded by the Department of Energy. The Government has certain rights in the invention.

FIELD OF THE INVENTION

The disclosed invention is in the field of isomerization of sugars.

BACKGROUND

Carbohydrate-based chemical processes are of growing importance in view of the desire to use renewable feedstocks such as biomass. The isomerization of sugars is an important class of reactions used in various industrial carbohydrate-based processes. The conversion of glucose into fructose is one such process of particular significance. This reaction has been used for the production of high-fructose corn syrups (HFCS) as well as for the production of valuable chemical intermediates, such as 5-hydroxymethylfurfural (HMF) and levulinic acid.

The isomerization of glucose to fructose can be performed under mild conditions using either biological or chemical catalysts. This reaction is slightly endothermic ($\Delta H=3$ kJ/mol) and reversible ($K_{eq} \sim 1$ at 298 K), which means that the maximum attainable degree of conversion of glucose to fructose is governed by the thermodynamic equilibrium between both sugars at the reaction temperature.

Industrial glucose isomerization is generally accomplished using an immobilized enzyme, which offers the benefit of high conversion and selectivity, but also presents numerous challenges. The enzymatic catalysts do not maintain high activity over multiple cycles, cannot be easily regenerated, and do not perform over a wide variety of temperatures, pHs, salt concentrations, and other process conditions. Furthermore, enzymatic isomerization catalysts cannot be easily integrated into upstream processes for forming glucose from biomass, or into downstream processes for transforming fructose into other chemical intermediates.

For example, one preferred industrial isomerization method involves the use of an immobilized enzyme (xylose isomerase) at 333 K that generates an equilibrium mixture of 42% (wt/wt) fructose, 50% (wt/wt) glucose, and 8% (wt/wt) other saccharides. Although fructose yields are high, this enzymatic process has various drawbacks that include: (i) the need for various prereaction purification processes to remove impurities from the feed that strongly inhibit enzyme activity, e.g., calcium ions present from a previous starch liquefaction/saccharification step must be removed to levels <1 ppm, (ii) the use of buffered solutions to maintain an optimal pH between 7.0 and 8.0 ($Na_2CO_3$) and to activate the enzyme ($MgSO_4$) that requires postreaction ion-exchange procedures, (iii) an optimal operating temperature of 333 K to maximize both product yield and enzyme lifetime that precludes faster reaction rates that could be attained at more elevated temperatures, and (iv) higher operating costs resulting from the periodic replacement of the catalyst bed due to the irreversible decay in activity suffered by the enzyme over time.

Accordingly, it is desirable to provide a process for isomerizing sugars with high conversion and selectivity without the drawbacks associated with enzymatic catalysts.

SUMMARY

In meeting the described challenges, processes are disclosed herein including processes for isomerizing a monosaccharide including contacting the monosaccharide in aqueous medium with a high-silica zeolite containing tin or titanium, incorporated into the framework of the zeolite, the zeolite having pores capable of admitting the monosaccharide. Processes are also disclosed for isomerizing a monosaccharide including contacting the monosaccharide in aqueous medium with an ordered mesoporous silica material containing tin or titanium, incorporated into the framework of the material.

Further processes are also disclosed for converting glucose to 5-hydroxymethylfurfural including contacting glucose in aqueous medium with a high silica zeolite containing tin or titanium, incorporated into the framework of the zeolite, the zeolite having pores capable of admitting the glucose, to provide fructose; and dehydrating the fructose. Still further processes are disclosed for converting starch to 5-hydroxymethylfurfural including hydrolyzing the starch in acid to provide glucose in an acidic aqueous medium; contacting glucose in aqueous medium with a high silica zeolite containing tin or titanium, incorporated into the framework of the zeolite, the zeolite having pores capable of admitting the glucose, to provide fructose; and dehydrating the fructose.

The general description and the following detailed description are exemplary and explanatory only and are not restrictive of the invention, as defined in the appended claims. Other aspects of the present invention can be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIGS. 8-11 depict scanning electron microscope images of titanium zeolite beta (FIGS. 8-9) and tin zeolite beta (FIGS. 10-11).

FIG. 14 depicts Sn-Beta before the reaction, and FIG. 15 depicts Sn-Beta after exposing Sn-Beta to glucose at a molar ratio of 200, 1:3 water to THF volume ratio, pH of 1 in HCl, 35 g of NaCl in 100 g of water.

FIG. 18 depicts a schematic representation of the glucose isomerization mechanisms by way of (A) proton transfer and (B) intramolecular hydride shift.

FIG. 32 depicts $^1$H NMR spectra of a) unlabeled glucose, b) labeled glucose-D2, c) glucose fraction obtained after reacting glucose-D2 with Sn-Beta, d) glucose fraction obtained after reacting labeled glucose-D2 with NaOH, e) unlabeled fructose, f) fructose fraction obtained after reacting labeled glucose-D2 with Sn-Beta, and g) fructose fraction obtained after reacting labeled glucose-D2 with NaOH.

FIGS. 43 and 44 provide reactivity data, and FIG. 45 provides X-ray diffraction (XRD) data before and after exposure to HCl at a pH of 1.

DETAILED DESCRIPTION OF ILLUSTRATIVE EMBODIMENTS

Figure 1:
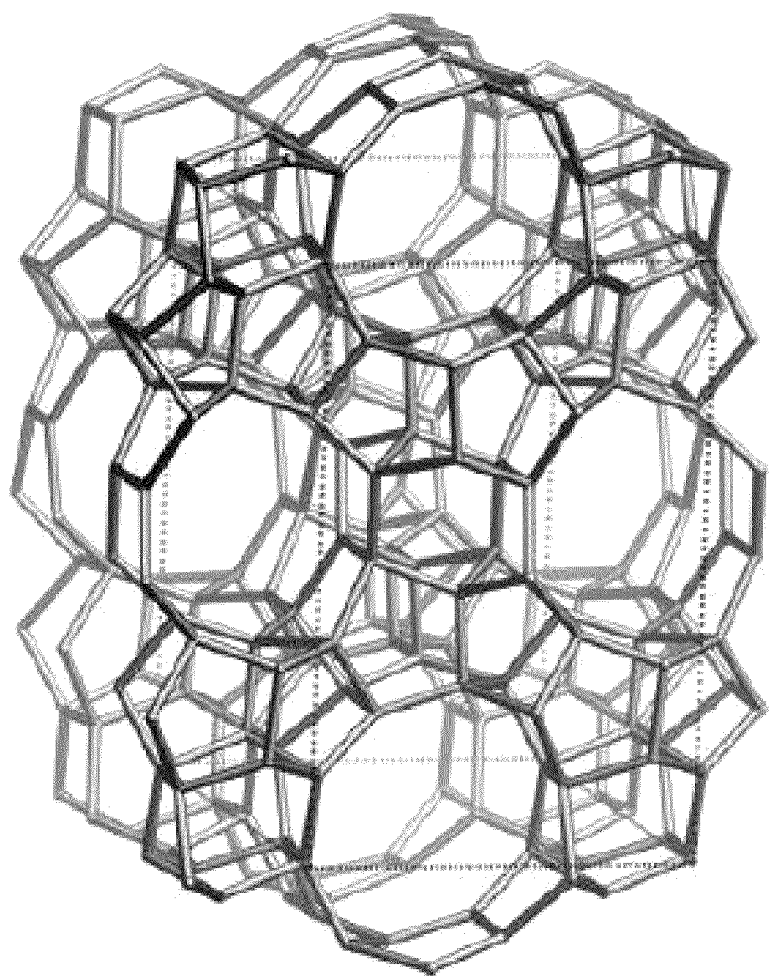
FIGS. 1-3 depict the structures and pore sizes of several different materials synthesized and tested for sugar isomerization activity.
Figure 2:
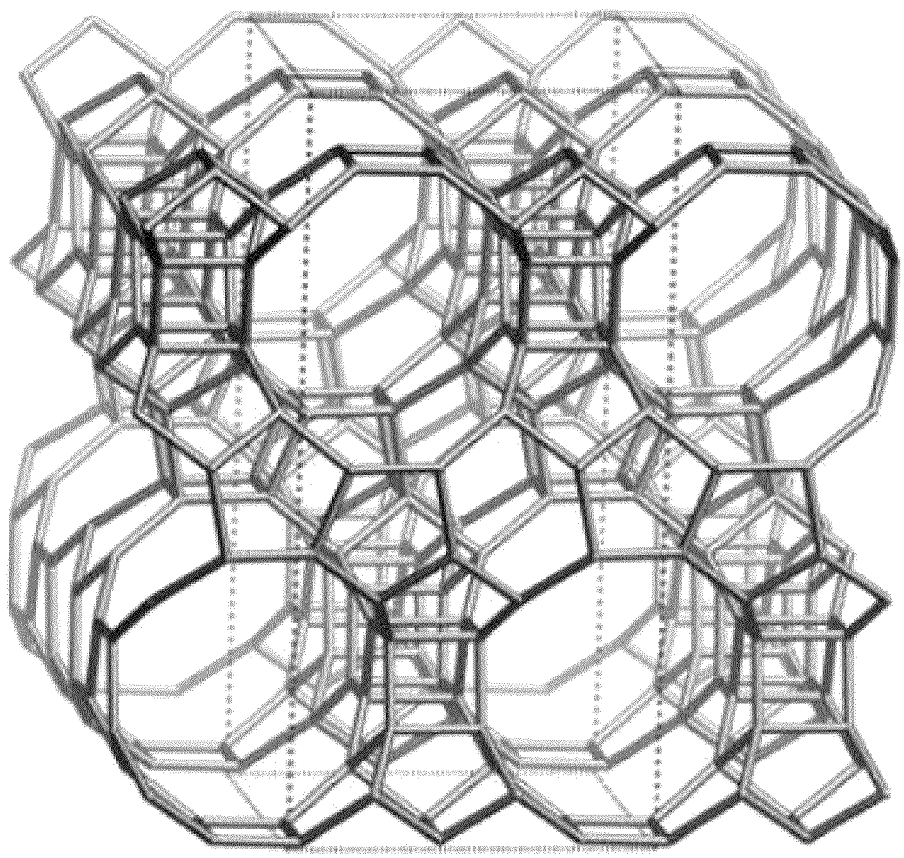
Figure 3:
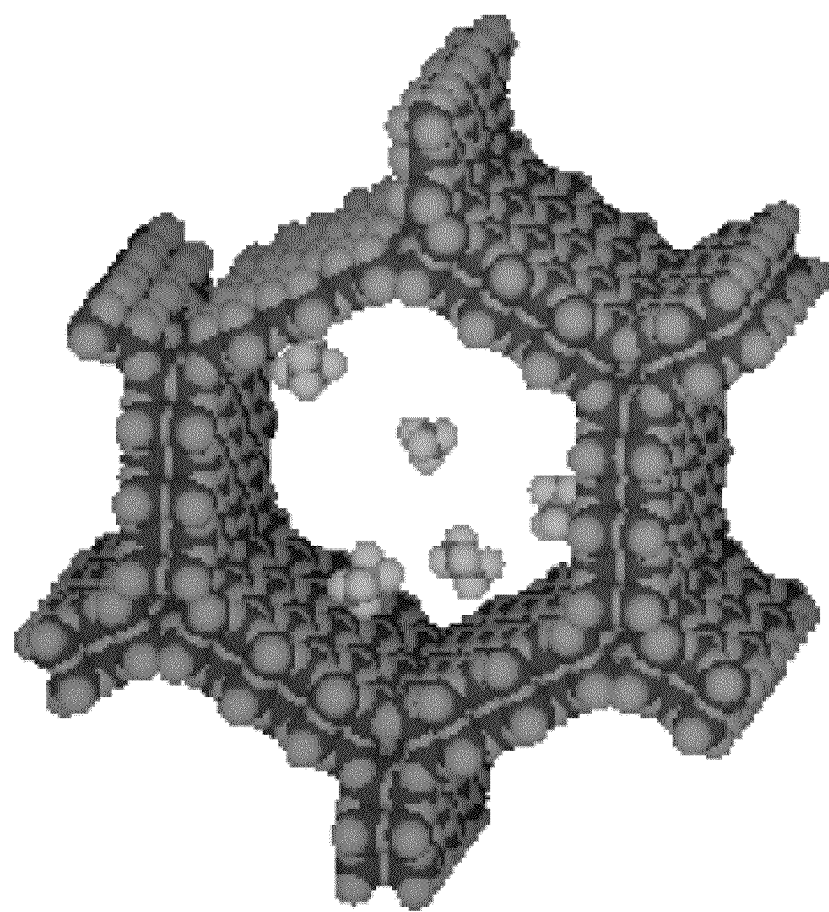
Figures 4, 5:
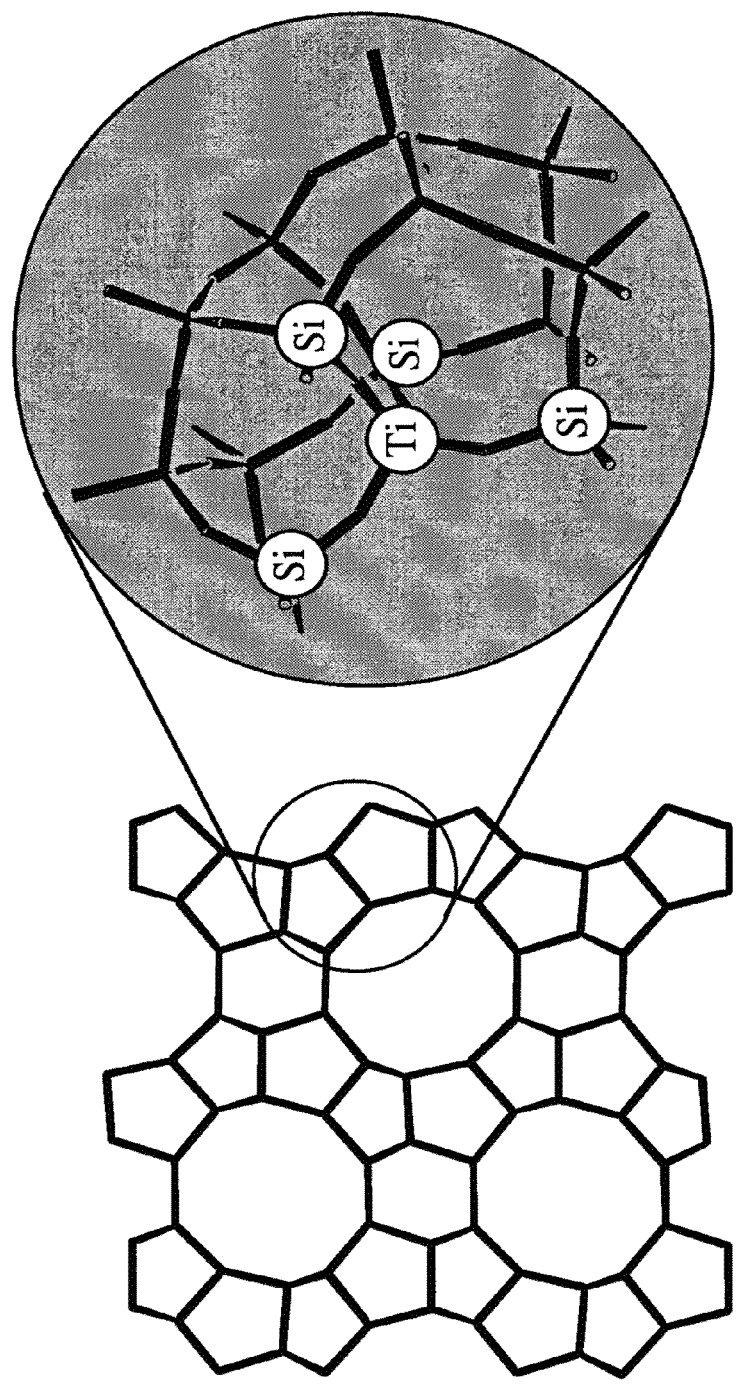
FIGS. 4-5 depict a zeolite structure containing titanium in the framework.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As used herein, when characterizing chemical reactivity of reactant x to form product y, conversion is defined as the moles of x reacted divided by the initial moles of x. Selectivity is defined as the moles of y produced divided by the moles of x reacted. Yield is defined as the moles of y produced divided by the initial moles of x. These quantities can be described fractionally or as percentages. For example, to describe conversion as a percentage, the moles of x reacted divided by the initial moles of x, and the result is multiplied by 100. It should be understood that unless otherwise noted, values of these quantities between 1 and 100 reflect percentages, not fractions.

In several processes disclosed herein, sugars are isomerized using chemical catalysis. As compared to biological catalysis, chemical catalysis employing inexpensive inorganic materials to isomerize sugars may offer attractive advantages, including operation over a wider range of temperatures and longer lifetimes, faster reaction rates that could give shorter reactor residence times, and a higher resistance to impurities.

For example, glucose undergoes isomerization in the presence of base catalysts at temperatures ranging from 298 to 423 K; unfortunately, monosaccharides are unstable in alkaline media and readily degrade into numerous byproducts at temperatures above 313 K. Thus, base catalysts typically generate fructose yields <10% (high-fructose selectivities [>90%] are only afforded at low glucose conversions [<10%]), thereby making them unlikely candidates for use in large-scale glucose processing.

Several processes disclosed herein make use of tin (Sn) or titanium (Ti) metal centers that can act as solid acids in aqueous media when incorporated in the framework of a siliceous material. For example, large-pore zeolites containing these types of acid centers are active in the isomerization of aldoses, such as glucose, while preventing sugar degradation reactions usually encountered in base-catalyzed processes.

The use of metal acid centers may take advantage of strong interactions between these types of metal centers and hydroxyl/carbonyl moieties that are present in aldoses. Indeed, recent reports have shown that Sn-Beta zeolites are highly active in the Meerwein-Ponndorf-Verley (MPV) reduction of carbonyl compounds, whereby a hydride transfer occurs from the hydroxyl group of an alcohol to the carbonyl group of a ketone. Corma A., et al. (2002) Al-free Sn-Beta zeolite as a catalyst for the selective reduction of carbonyl compounds (Meerwein-Ponndorf-Verley reaction), J. Am. Chem. Soc. 124(13):3194-95. Similarly, others have shown that Sn-containing materials catalyze the conversion of trioses, e.g., glyceraldehyde and dihydroxyacetone, into alkyl lactates by way of a Lewis-acid mediated isomerization/esterification reaction sequence in the presence of alcohols. Hayashi Y. & Sasaki Y. (2005) Tin-catalyzed conversion of trioses to alkyl lactates in alcohol solution, Chem. Commun. 21:2716-18; Taarning E, et al. (2009) Zeolite-catalyzed isomerization of triose sugars, ChemSusChem 2(7):625-27.

In several methods disclosed herein, a monosaccharide is isomerized by, among other things, contacting the monosaccharide in aqueous medium with a catalyst. The catalyst may be, for example, an inorganic material containing metal centers.

In further methods disclosed herein, the inorganic material may be a siliceous material. The inorganic material may also be a porous material, or in particular a molecular sieve, or in particular a microporous material such as a zeolite. For example, the inorganic material may be a high-silica zeolite.

Although many zeolites are aluminosilicates, zeolites incorporating other constituents, for example zinc, are known in the art, as are methods for synthesizing them. Some zeolites are termed high-silica, meaning that the ratio of silicon to aluminum in the framework is high, for example at least 10:1, or as high as 100:1 or even higher. High-silica zeolites may even be entirely free of aluminum. The higher the ratio of silicon to aluminum, the more neutral and hydrophobic the framework of the zeolite becomes.

In embodiments where the inorganic material is a porous material, the pores of the material may be designed such that the pores are sufficiently large to admit monosaccharide or other reactants or products to the interior of the porous material. For example, where the inorganic material is a zeolite, a particular zeolite with a desired pore size may be selected. Pore size is one way to classify zeolites, and zeolites of a variety of pore sizes are known in the art. The pore size of the zeolite may also be selected to exclude undesirable or interfering molecules.

In embodiments where the inorganic material is a porous material, the material may be designed such that the catalyst reactivity is afforded inside the material, whereby the reactants enter the material through the pores, react to form products, and then the products leave the material through the pores. In still further embodiments, surface reactivity may be present, but it may also be insubstantial, negligible, or entirely absent. In some examples, the inorganic material may contribute to the catalytic activity, but in others, the metal centers provide the catalytic activity.

In further methods disclosed herein, the metal centers are incorporated into the framework of the inorganic material. For example, zeolites may contain metals within the framework of the zeolite. Examples of such zeolites are known in the art. E.g., Corma A. et al. (2001) Sn-zeolite beta as a heterogeneous chemoselective catalyst for Baeyer-Villiger oxidations, Nature 412(6845):423-25. Notwithstanding this knowledge, successful incorporation of metals into the framework of a zeolite generally should be proven by characterization of the zeolite.

In still further methods disclosed herein, the metal centers act as Lewis acids. In such methods, the metal may lend Lewis acid activity to the inorganic material. A number of metals are known generally in the prior art to act as Lewis acids, depending upon whether they are present as cations, complexes, or covalent compounds, for example aluminum, boron, chromium, cobalt, iron, titanium, tin, and others. In some methods disclosed herein, for example, the metal centers are tin or titanium. Other metals known in the art to have Lewis acid activity are also contemplated for incorporation into the catalyst.

In further methods disclosed herein, the catalyst may be a zeolite containing tin or titanium incorporated into the framework of the zeolite. For example, the catalyst may be a high-silica zeolite containing tin or titanium incorporated into the framework of the zeolite.

In several of the methods disclosed herein, the catalyst includes zeolite beta. Generally, zeolite beta is a zeolite defined by the topology *BEA, the characteristics of which are set forth, for example, in the Atlas of Zeolite Framework Types, Sixth Edition (Baerlocher et al., 2007). Other zeolites known in the art are contemplated. The choice of zeolite depends upon the appropriate framework size, shape, and constituents, depending upon the reaction to be catalyzed, reactants, and products. For example, where the reaction to be catalyzed is the isomerization of glucose to form fructose, a zeolite with pore sizes capable of admitting glucose and fructose is desirable, for example, zeolite beta. Larger reactants and products would call for materials with proportionately larger pores.

In other methods disclosed herein, the catalyst includes zeolites such as TS-1, which is a titanosilicate material with the MFI topology. Various other large pore and extra-large pore zeolites are contemplated as well, for example CIT-1, ZSM-12, SSZ-33, SSZ-26, CIT-5, or high silica FAU.

In still further methods disclosed herein, the porous material is an ordered mesoporous silica material. For example, a monosaccharide is isomerized by, among other things, contacting the monosaccharide in aqueous medium with an ordered mesoporous silica material containing tin or titanium, incorporated into the framework of the material. The mesoporous silica material may be, for example, MCM-41, SBA-15, TUD-1, HMM-33 or FSM-16.

In yet further methods disclosed herein, the catalyst is contacted with the monosaccharide in aqueous solution, meaning a solution where the solvent is water. The catalysts disclosed herein may be contacted with monosaccharide in other solvents, for example alcohols, although as disclosed elsewhere herein, the choice of solvent significantly impacts the outcome of the chemical reaction.

In further methods disclosed herein, the catalyst is contacted with a carbohydrate. For example, the catalyst may be contacted with a monosaccharide, disaccharide, trisaccharide, oligosaccharide or polysaccharide. Furthermore, any combination of carbohydrates may be contacted with the catalyst as appropriate. Furthermore, carbohydrates of any chirality may be contacted with the catalyst.

Where the carbohydrate is a monosaccharide, the monosaccharide may be an aldose, such as an aldotriose, aldotetrose, aldopentose or aldohexose. In particular, the aldoses may include glyceraldehyde, erthrose, threose, ribose, arabinose, xylose, lyxose, allose, altrose, glucose, mannose, gulose, idose, galactose or talose.

Also where the carbohydrate is a monosaccharide, the monosaccharide may be a ketose, such as a ketotriose, ketotetrose, ketopentose, or ketohexose. In particular, the ketoses may include dihydroxyacetone, erythrulose, ribulose, xylulose, psicose, fructose, sorbose, or tagatose.

Other monosaccharides and derivatives thereof may also be contacted with the catalysts disclosed herein, including pyranoses, furanoses, amino sugars, and the like.

Where the carbohydrate is a disaccharide, the disaccharide may be any combination of monosaccharides, for example sucrose, lactulose, lactose, maltose, trehalose, cellobiose, kojibiose, nigerose, isomaltose, sophorose, laminarbiose, gentiobiose, turanose, maltulose, palatinose, gentiobiulose, mannobiose, melibiose, melibulose, rutinose, rutinulose or xylobiose.

Mixtures of carbohydrates may also be contacted with the catalysts disclosed herein, including mixtures of carbohydrates that are the byproduct of hydrolysis reactions of biomass materials such as starch and cellulose, for example maltose and cellobiose. Furthermore, oligosaccharides and polysaccharides may be contacted with the catalysts disclosed herein, for example fructo-oligosaccharides and galacto-oligosaccharides, as well as starches, celluloses, and chitins.

In further methods disclosed herein, the aqueous medium includes between about 0.001 weight percent monosaccharide and the maximum solubility of the monosaccharide in the medium at a selected temperature. For example, the aqueous medium may include between about 0.001 weight percent monosaccharide and about 50 weight percent monosaccharide, or between about 10 weight percent monosaccharide and about 50 weight percent monosaccharide. The aqueous medium may also include between about 25 weight percent monosaccharide and about 50 weight percent monosaccharide. Higher concentrations are industrially desirable because of the increased utilization of processing equipment, among other reasons. The particular monosaccharide concentration selected depends in part on the solubility of the monosaccharide selected.

Figure 46:
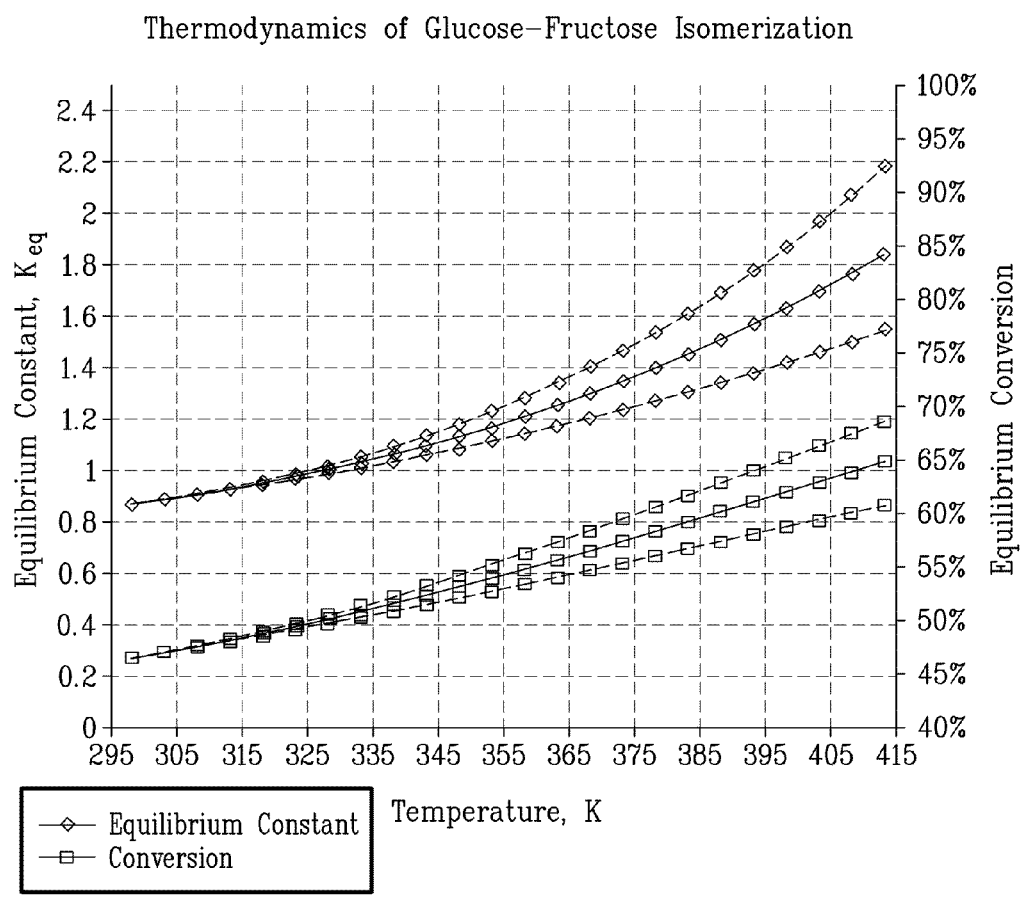
FIG. 46 depicts thermodynamic data of glucose to fructose isomerization based on data from Tewari, Y., Applied Biochemistry and Biotechnology 1990, 23, 187.

In further methods disclosed herein, the isomerization reaction substantially reaches thermodynamic equilibrium. For example, in the conversion of glucose to fructose, the equilibrium conversions are depicted in FIG. 46. In still further methods disclosed herein, the isomerization reaction is performed by a chemical catalyst that provides substantially the same conversion and selectivity as prior art enzymatic systems.

In yet other methods disclosed herein, the pH of the aqueous medium is acidic, meaning less than 7.0. Although monosaccharides may be isomerized in non-acidic conditions, for example as disclosed herein, isomerization in acid conditions, also disclosed herein, has notable utility. Indeed, the ability to isomerize sugars in an acidic solution is essential to overcome some of the main bottlenecks encountered during base catalysis, some of which include the neutralization of active sites by acidic byproducts and the low stability of sugars in alkaline environments. Furthermore, working at low pH values affords opportunities to couple upstream and downstream acid-catalyzed reactions, e.g., hydrolysis or dehydration, with the glucose isomerization reaction without the need to use additional unit operations. For example, in the production of high fructose corn syrup (HFCS), the starch hydrolysis step (typically performed in a separate set of reactors using either acid catalysts or a combination of enzymes) required prior to the isomerization step could be combined with the glucose isomerization step. Similarly, in the production of HMF, the base-catalyzed isomerization step required to convert glucose into fructose before performing the acid-catalyzed dehydration step could be combined in a single reactor to obtain higher product yields more efficiently.

In some methods disclosed herein, the pH of the aqueous medium is between about 0 and about 4. In further methods disclosed herein, the pH of the aqueous medium is between about 0 and about 2. A pH of between about 0 and about 2, including 2, is particularly useful for coupling isomerization with the hydrolysis of starch and/or the dehydration of fructose to form HMF.

In still other methods disclosed herein, the aqueous medium comprises a salt. Salt may be present for a number of reasons, for example, it may be carried over from a previous process, and salt tolerance may be advantageous for economic and efficiency reasons. As another example, salt may also be added intentionally in order to facilitate partitioning across multiple liquid phases. In some methods disclosed herein, the salt may include a cation which could be any metal, for example sodium, potassium, magnesium, calcium, lithium or others. The salt may likewise include an anion such as acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate or bis-trifluorsulfonimide. For example, the salt may be sodium chloride, potassium chloride, magnesium chloride, or potassium bromide.

In yet other methods disclosed herein, the isomerization is carried out at a temperature of between about 50° C. and about 250° C. The choice of temperature influences reaction kinetics as well as conversion and selectivity. Depending upon the composition of the aqueous solution, the maximum temperature for the reaction may depend upon whether the reactor is pressurized, and if so, to what pressure. For example, the isomerization may be carried out at a temperature of between about 90° C. and about 180° C. As a further example, the isomerization may be carried out at a temperature of between about 90° C. and about 140° C. Where feasible, lower temperatures may be desirable to conserve energy.

In further methods disclosed herein, the isomerization may be carried out for less than about 90 minutes. In general, a reaction must be allowed to proceed long enough to reach a desired conversion. Shorter reaction times may be desirable from an industrial point of view for efficiency reasons. For example, the isomerization may be carried out for less than about 60 minutes, or less than about 30 minutes. Another reason to use shorter reaction times is the potential for the buildup of undesirable degradation products.

In still further methods disclosed herein, the conditions of the monosaccharide isomerization reaction are selected such that a zeolite catalyst may be used batchwise for at least three reaction cycles without significant reduction in performance and without the need for calcination. A stable catalyst offers several advantages of industrial importance, including increased efficiency, reduced cost, and reliability. In some methods disclosed herein, a Sn-Beta catalyst is stable and maintains its activity both after reuse and after calcination. For example, successive cycles of glucose isomerization were performed with no intermediate treatment of the catalyst, and conversion and selectivity were maintained. In other examples disclosed herein, even where the catalyst suffers decreased performance, a step of calcining in air in between cycles restores performance. Whether the catalyst suffers decreased performance may depend, in part, upon the choice of catalyst and the choice of reaction conditions. For example, where the reaction time and temperature are kept to modest levels, for example 383K and 30 minutes, no intermediate step of calcining is necessary.

In further methods disclosed herein, the product of the monosaccharide isomerization is then dehydrated. For example, the dehydration may be conducted to form furan derivatives useful as chemical intermediates. As a further example, glucose is converted to 5-hydroxymethylfurfural (HMF) by, among other things, contacting glucose in aqueous medium with a high silica zeolite containing tin or titanium, incorporated into the framework of the zeolite, the zeolite having pores capable of admitting the glucose, to provide fructose and then dehydrating the fructose.

In other aspects combining isomerization and dehydration disclosed herein, the catalyst includes zeolites such as Beta. Various other large pore and extra-large pore zeolites are contemplated as well, for example CIT-1, ZSM-12, SSZ-33, SSZ-26, CIT-5, or high silica FAU. In still further methods combining isomerization and dehydration disclosed herein, the porous material is an ordered mesoporous silica material. For example, a monosaccharide is isomerized by, among other things, contacting the monosaccharide in aqueous medium with an ordered mesoporous silica material containing tin or titanium, incorporated into the framework of the material. The mesoporous silica material may be, for example, MCM-41, SBA-15, TUD-1, HMM-33 or FSM-16.

In further aspects disclosed herein, the product of the monosaccharide isomerization may be maintained in the aqueous medium while it is dehydrated. For example, fructose may be maintained in the aqueous medium while it was dehydrated. This procedure offers the benefit of obviating the need for a separation step, instead conducting both the isomerization and dehydration reactions in the same aqueous medium. The methods disclosed herein are particularly suitable for such a procedure, because certain isomerization catalysts disclosed herein are stable in the conditions necessary for dehydration.

Generally, the dehydration of saccharides to form furan derivatives is well studied, and in particular the dehydration of fructose to form HMF is known in the art. In certain methods disclosed herein, the dehydration of the product of the isomerization reaction is carried out in the presence of an acid catalyst. For example, the catalyst may be an inorganic acid dissolved in the aqueous medium, such as HCl. The catalyst may also be, for example, a solid acid catalyst such as a protonated high silica zeolite having a *BEA topology. Other acid sources may be useful as well, such as cation exchange resins, lewis acids, silica-alumina materials, titania-alumina materials, mineral acids, heteropolyacids, nitric acid, sulfuric acid, phosphoric acid, boric acid, oxalic acid, levulinic acid, citric acid, niobium oxide, vanadium phosphate or niobium phosphate.

The isomerization and dehydration reactions may be carried out in sequence or simultaneously, or some combination of the two. For example, a monosaccharide is contacted with an isomerization catalyst and a dehydration catalyst in aqueous solution, both reactions can proceed together. In a particular example, if glucose is contacted with an isomerization catalyst in an acidic aqueous solution, the glucose reacts first to form fructose and then to form HMF. The particular reactions conditions may be, among others, any of the conditions disclosed in connection with isomerization.

In some methods combining isomerization and dehydration disclosed herein, the pH of the aqueous medium is between about 0 and about 4. In further methods disclosed herein, the pH of the aqueous medium is between about 0 and about 2. In still other methods combining isomerization and dehydration disclosed herein, the aqueous medium comprises a salt, for example including a cation which could be any metal, for example sodium, potassium, magnesium, calcium, lithium or others. The salt may likewise include an anion such as acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate or bis-trifluorsulfonimide. For example, the salt may be sodium chloride, potassium chloride, magnesium chloride, or potassium bromide.

In yet other methods disclosed herein, the isomerization is carried out at a temperature of between about 50° C. and about 250° C. The choice of temperature influences reaction kinetics as well as conversion and selectivity. Depending upon the composition of the aqueous solution, the maximum temperature for the reaction may depend upon whether the reactor is pressurized, and if so, to what pressure. For example, the isomerization may be carried out at a temperature of between about 90° C. and about 180° C. As a further example, the isomerization may be carried out at a temperature of between about 90° C. and about 140° C. Where feasible, lower temperatures may be desirable to conserve energy.

In further methods disclosed herein, the isomerization may be carried out for less than about 90 minutes. In general, a reaction must be allowed to proceed long enough to reach a desired conversion. Shorter reaction times may be desirable from an industrial point of view for efficiency reasons. For example, the isomerization may be carried out for less than about 60 minutes, or less than about 30 minutes. Another reason to use shorter reaction times is the potential for the buildup of undesirable degradation products.

In still other methods disclosed herein, the combination isomerization-dehydration reaction can be conducted in a biphasic system, for example as described in U.S. Pat. No. 7,572,925. A biphasic system involves two substantially immiscible liquid phases, one aqueous and one organic. A biphasic system in principle offers advantages for conversion, selectivity, and purification efficiency. In this application, the isomerization of the saccharide takes place in the aqueous phase, as does the dehydration of the isomerization product. For example, both the isomerization of glucose into the fructose and the dehydration of fructose into HMF take place in the aqueous phase. Furthermore, the catalysts for each of those reactions is provided in the aqueous phase. The dehydration product, for example HMF, is then extracted into the organic layer. Thus, for example, the aqueous medium may be contacted with an organic medium capable of extracting HMF from the aqueous medium, wherein the organic medium is substantially immiscible with the aqueous medium. This keeps the aqueous layer relatively free of HMF, thus improving the performance of the dehydration reaction, and provides HMF product in a relatively pure state in the organic layer, thus simplifying purification. Thus, for example, in some methods disclosed herein, the HMF is produced in the aqueous medium, and extracted from the aqueous medium to the organic medium as it is produced.

A wide variety of solvents may be used for the organic medium, for example any water-immiscible, linear, branched, or cyclic alcohol, ether, or ketone, or an unsubstituted aliphatic or aromatic hydrocarbon, or a halo-substituted aliphatic or aromatic hydrocarbon, or mixtures of any of the above. For example, in some aspects disclosed herein, the organic medium includes 1-butanol or THF. Some components of the organic layer may include compounds that are somewhat miscible with water. Other organic media components disclosed include, for example, DMSO, DMF, N-methylpyrrolidinone, acetonitrile, acetone, butanone, pentanone, hexanone, heptanone, and the like.

In yet further methods disclosed herein, several reactions are combined in order to convert starch to HMF. As is well known in the art, starch may be hydrolyzed by acid to form glucose. In accordance with this disclosure, the isomerization of glucose using catalysts disclosed herein performs well in acidic conditions. Thus, methods are disclosed herein for converting starch to 5-hydroxymethylfurfural by, among other things, hydrolyzing the starch in acid to provide glucose in an acidic aqueous medium, contacting glucose in aqueous medium with a high silica zeolite containing tin or titanium, incorporated into the framework of the zeolite, the zeolite having pores capable of admitting the glucose, to provide fructose, and dehydrating the fructose. These three reactions can be combined, for example, methods are disclosed including maintaining the glucose in the acidic aqueous medium while it is contacted with high silica zeolite to provide fructose. And likewise, methods are disclosed including maintaining the fructose in the acidic aqueous medium while it is dehydrated to provide 5-hydroxymethylfurfural. As a further example, all three reactions are conducted in one pot, in aqueous solution, whereby the initial reactant is starch and the final product is HMF.

In other methods disclosed herein, the conversion of starch to HMF can be effected in a biphasic system, for example in accordance with U.S. Pat. No. 7,572,925. All of the variations and disclosure applicable to the isomerization reaction and to the combination of the isomerization and dehydration reactions, whether in aqueous solution or in a biphasic system, are applicable to the starch to HMF system. Thus, for example, the acidic aqueous medium is contacted with an organic medium capable of extracting 5-hydroxymethylfurfural from the acidic aqueous medium, wherein the organic medium is substantially immiscible with the aqueous medium. And in a further example, 5-hydroxymethylfurfural is produced in the acidic aqueous medium, and extracted from the aqueous medium to the organic medium as it is produced.

EXAMPLES AND FURTHER EMBODIMENTS

Example 1

Ti-Beta zeolite was prepared as follows: 7.503 g of tetraethylammonium hydroxide solution (Sigma-Aldrich, 35% wt in water) were diluted with 15 g of water. Then, 7.016 g of tetraethylorthosilicate (Sigma-Aldrich, 98% wt) and 0.201 g of titanium (IV) isopropoxide (Sigma-Aldrich, 97% wt) were added to the solution. The mixture was stirred until complete hydrolysis of the tetraethylorthosilicate and titanium (IV) isopropoxide, allowing evaporation of ethanol, isopropanol and required water until desired water ratio. Finally, 0.670 g of HF solution (Mallinckrodt, 52% wt in water) were added resulting in a thick gel.

The gel composition was $SiO_2/0.021\ TiO_2/0.54\ TEAOH/0.53\ HF/6.6\ H_2O$. This gel was transferred to a Teflon-lined stainless steel autoclave and heated at 140° C. for 14 days. The solids were recovered by filtration, extensively washed with water, and dried at 100° C. overnight. The solid material shows the Beta zeolite topology (see Ti-Beta XRD pattern in FIG. 13). The solid is calcined at 580° C. for 6 hours to remove the organic content located into the crystalline material. UV-vis diffuse reflectance spectrum of the calcined sample shows the presence of a unique band at ~200-250 nm, which can be assigned to Ti tetrahedrally coordinated into the zeolite framework (see Ti-Beta in FIG. 12).

Example 2

Sn-Beta zeolite was prepared as follows: 7.57 g of tetraethylammonium hydroxide solution (Sigma-Aldrich, 35 wt % in water) was diluted with 15 g of water. Next, 7.011 g of tetraethylorthosilicate (Sigma-Aldrich, 98 wt %) and 0.121 g of tin (IV) chloride pentahydrate (Sigma-Aldrich, 98 wt %)

were added to the solution. The mixture was stirred until complete hydrolysis of the tetraethylorthosilicate was obtained, and then allowed to reach the desired water ratio by complete evaporation of ethanol and some water. Finally, 0.690 g of HF solution (Mallinckrodt, 52 wt % in water) was added resulting in a thick gel.

Figure 6:
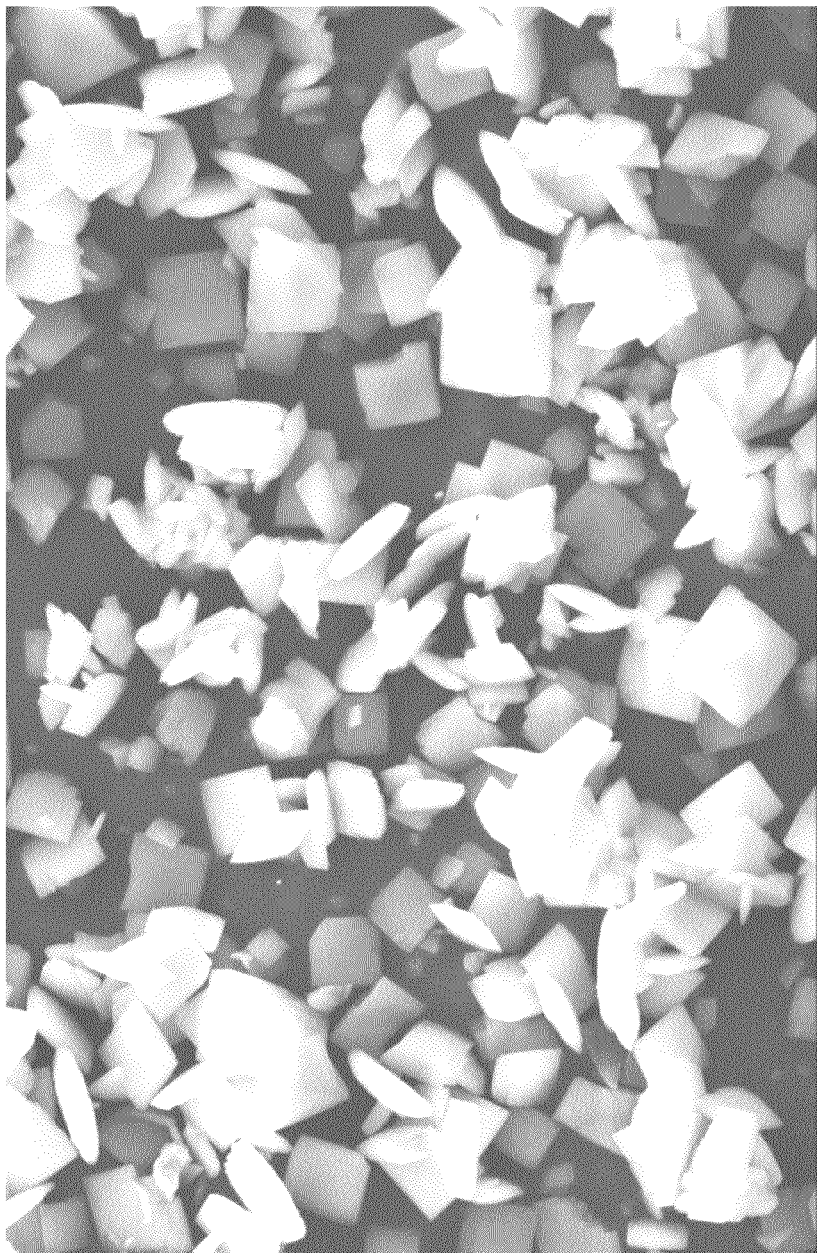
FIG. 6 depicts a scanning electron microscope image of tin zeolite beta.
Figure 7:
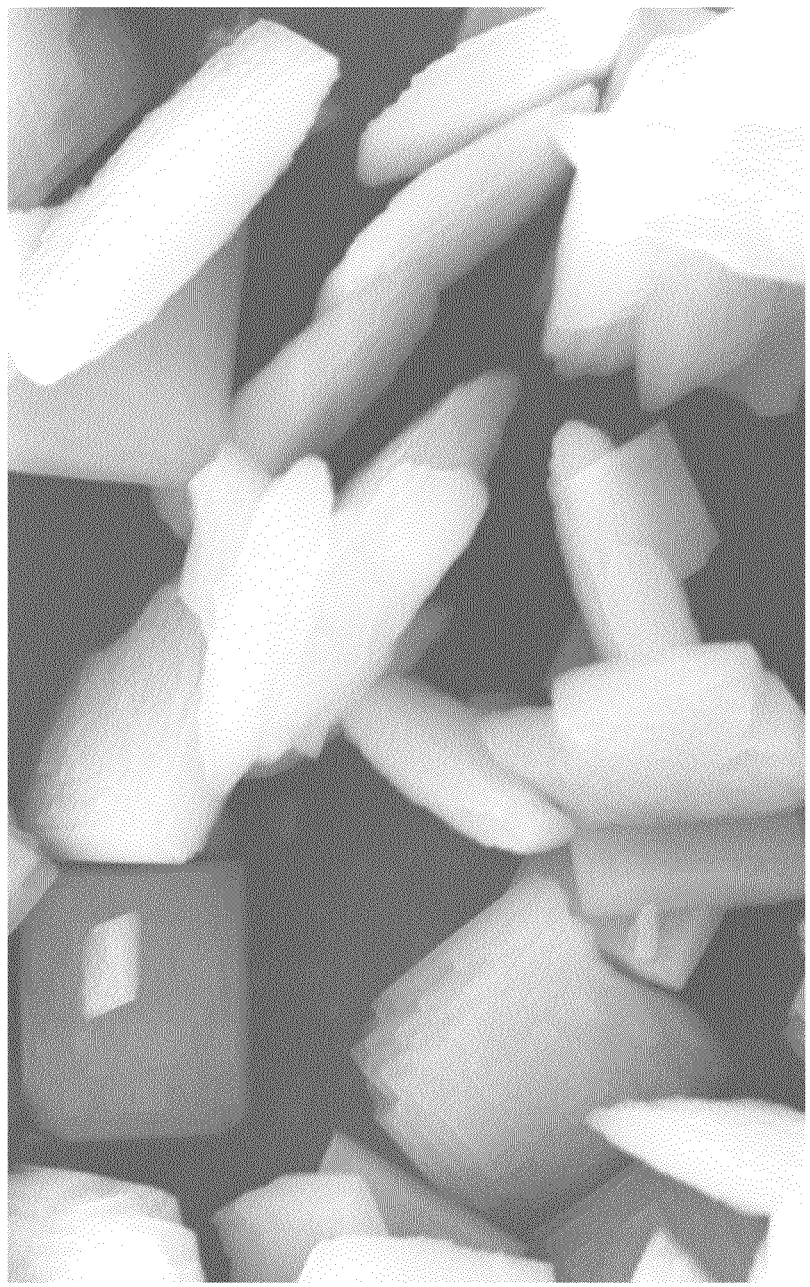
FIG. 7 depicts a scanning electron microscope image of tin zeolite beta.

The gel composition was $SiO_2/0.01\ SnCl_4/0.55\ TEAOH/0.54\ HF/7.52\ H_2O$. This gel was transferred to a Teflon-lined stainless steel autoclave and heated at 140° C. for 50 days. The solids were recovered by filtration, extensively washed with water, and dried at 100° C. overnight. The solid was calcined at 580° C. for 6 hours to remove the organic content located into the crystalline material. X-ray diffraction confirmed that the solid material has the Beta zeolite topology (see Sn-Beta XRD pattern in FIG. 13). UV-vis diffuse reflectance spectrum of the calcined sample shows the presence of a unique band at ~200-250 nm, which can be assigned to Sn tetrahedrally coordinated into the zeolite framework (see Sn-Beta in FIG. 12). Scanning electron microscopy (SEM) shows the Sn-Beta crystals are several microns in size, FIGS. 6-7, and energy dispersive X-ray spectroscopy (EDS) measurements for the Sn-Beta sample show an atomic ratio Si:Sn of 96:1.

Example 3

TS-1 was synthesized following the method reported in the patent literature (U.S. Pat. No. 4,410,501). TS-1 was crystallized from a clear solution prepared by mixing titanium butoxide (TNBT, Sigma-Aldrich), tetraethylorthosilicate (TEOS, Sigma-Aldrich), tetrapropylammonium hydroxide (TPAOH, 1M, Sigma-Aldrich) and distilled water. The mixture was stirred until complete hydrolysis of the tetraethylorthosilicate and titanium butoxide was obtained, then allowing complete evaporation of ethanol, butanol and some water until the desired water ratio was reached. The gel composition was $SiO_2/0.03\ TiO_2/0.44\ TPAOH/30\ H_2O$. The TS-1 reaction mixture was charged into Teflon-lined autoclaves and allowed to crystallize at 175° C. for 5 days. The autoclave was rotated at 50 RPM. After cooling, the solid was recovered by filtration, extensively washed with water, and dried at 100° C. overnight. The material was calcined at 580° C. for 6 hours to remove the organic content located within the crystalline material.

Example 4

The Ti-MCM-41 sample was synthesized as follows: a solution of hexadecyltrimethylammonium bromide (C16TABr) was prepared (1.93 g of C16TABr in 15.1 g of water). Then, 6.42 g of tetramethylammonium hydroxide solution (25%, Aldrich) was added. After homogenization, 7.015 g of tetraethylorthosilicate (Sigma-Aldrich, 98% wt) and 0.19 g of titanium (IV) isopropoxide (Sigma-Aldrich, 97% wt) were added to the solution. The mixture was stirred until complete hydrolysis of the tetraethylorthosilicate and titanium (IV) isopropoxide was obtained. Next, complete evaporation of ethanol, isopropanol and some water was allowed until the desired water ratio was reached. The final composition was: $1.0\ SiO2/0.02\ TiO_2/0.16\ C_{16}TABr/0.26\ TMAOH/24.8\ H_2O$. The homogeneous gel was sealed in Teflon-lined stainless steel autoclaves and heated at 135° C. under static conditions during 48 hours. The solid was recovered by filtration, extensively washed with water, and dried at 100° C. overnight. The solid was calcined at 580° C. for 6 hours to remove the organic content located within the ordered material.

Example 5

The Sn-MCM-41 sample was synthesized as follows: a solution of hexadecyltrimethylammonium bromide (C16TABr) was prepared (1.46 g of C16TABr in 4.3 g of water). Then, 6.34 g of tetramethylammonium hydroxide solution (25%, Aldrich) was added. After homogenization, 0.088 g $SnCl_4.5H_2O$ (98%, Aldrich) and 3.76 g of colloidal silica solution (Ludox AS-40, Sigma-Aldrich) were added with continuous stirring. The final composition was: $1.0\ SiO_2/0.01\ SnCl4/0.16\ C_{16}TABr/0.35\ TMAOH/25\ H_2O$. The homogeneous gel was sealed in Teflon-lined stainless steel autoclaves and heated at 135° C. under static conditions during 48 hours. The solid was recovered by filtration, extensively washed with water, and dried at 100° C. overnight. The solid was calcined at 580° C. for 6 hours to remove the organic content located within the ordered material.

Example 6

Various materials were synthesized using known methods. The following table lists several materials synthesized along with the silicon/metal ratio, which was measured by Energy Dispersive X-ray Spectroscopy (EDS).

| Material | Metal | Si/Metal |
| --- | --- | --- |
| Ta-Beta [1] | Ta | 102.0 |
| TS-1 [2] | Ti | 34.7 |
| Ti-Beta | Ti | 53.8 |
| Ti-MCM-41 [3] | Ti | 64.4 |
| Sylilated-MCM-41 [4] | Ti | 64.4 |
| Sn-Beta | Sn | 70.2 |
| Sn-MCM-41 [5] | Sn | 71.8 |

The syntheses of these materials are described as disclosed in examples 1-5, in accordance with the literature as noted: [1] Corma, A. et al., J. Phys. Chem. C, 2009, 113 (26), pp. 11306-11315; [2] C. B. Khouw, H. X. Li and M. E. Davis, Micropor. Mater. 2. (1994), p. 425; [3] Blasco et al., J. Catal., 1995, 156, p. 65; [4] Ti-MCM-41 sample was treated with hexamethyldisilazane for capping the silanols on surface; [5] Corma, A. et al., ARKIVOC, 2005, ix, p. 124.

Powder X-ray diffraction (XRD) patterns were collected by using a Scintag XDS 2000 diffractometer using Cu Ka radiation. Scanning electron microscopy (SEM) with Energy Dispersive X-ray Spectroscopy (EDS) measurements were recorded on a LEO 1550 VP FE SEM at an electron high tension (EHT) of 10 kV. UVVis measurements were recorded using a Cary 3G spectrophotometer equipped with a diffuse reflectance cell.

Example 7

Glucose isomerization experiments were carried out in 10 ml thick-walled glass reactors (VWR) heated in a temperature-controlled oil bath placed on top of an digital stirring hotplate (Fisher Scientific). In a typical experiment, 1.5 g of an aqueous solution composed of 10 wt % glucose and the corresponding catalyst amount to achieve a 1:50 metal:glucose molar ratio (typically ~70 mg) were added to the reactor and sealed. The reactor was placed in the oil bath and removed at specific times. The reaction was stopped by cooling the reactor in an ice bath, and small aliquots were taken for analysis. Sample analyses were performed by means of high performance liquid chromatography (HPLC) using a Agilent 1200 system (Agilent Technologies Corp.) equipped with PDA UV (320 nm) and evaporative light-scattering (ELS)

detectors. Glucose and fructose concentrations were monitored with a Phenomenex RHM column (Phenomenex), using ultrapure water (pH=7) as the mobile phase at a flow rate of 0.55 ml/min and a column temperature of 353 K.

Example 8

The following table summarizes the results of glucose isomerization experiments:

| Entry | Catalyst | Solvent | Temp. (° C.) | Time (min) | Glucose Conversion (%) | Fructose Selectivity (%) |
|---|---|---|---|---|---|---|
| 1a | — | $H_2O$ | 110 | 0 | 0 | — |
| 1b | — | $H_2O$ | 110 | 15 | 1.5 | 0 |
| 1c | — | $H_2O$ | 110 | 45 | 1.8 | 0 |
| 1d | — | $H_2O$ | 110 | 90 | 3.4 | 0 |
| 2a | HCl (pH = 2) | $H_2O$ | 110 | 0 | 0 | — |
| 2b | HCl (pH = 2) | $H_2O$ | 110 | 15 | 1 | 0 |
| 2c | HCl (pH = 2) | $H_2O$ | 110 | 45 | 1.4 | 0 |
| 2d | HCl (pH = 2) | $H_2O$ | 110 | 90 | 2 | 0 |
| 3a | Ti-Beta | $H_2O$ | 110 | 0 | 0 | — |
| 3b | Ti-Beta | $H_2O$ | 110 | 15 | 10.5 | 82.8 |
| 3c | Ti-Beta | $H_2O$ | 110 | 45 | 17.9 | 80.4 |
| 3d | Ti-Beta | $H_2O$ | 110 | 90 | 24.7 | 65 |
| 4a | Ti-Beta/HCl (pH = 2) | $H_2O$ | 110 | 0 | 0 | — |
| 4b | Ti-Beta/HCl (pH = 2) | $H_2O$ | 110 | 15 | 6.9 | 95 |
| 4c | Ti-Beta/HCl (pH = 2) | $H_2O$ | 110 | 45 | 15 | 90 |
| 4d | Ti-Beta/HCl (pH = 2) | $H_2O$ | 110 | 90 | 21.1 | 81.8 |
| 5a | Sn-Beta | $H_2O$ | 110 | 0 | 0 | — |
| 5b | Sn-Beta | $H_2O$ | 110 | 15 | 27.4 | 98 |
| 5c | Sn-Beta | $H_2O$ | 110 | 45 | 49.7 | 92 |
| 5d | Sn-Beta | $H_2O$ | 110 | 90 | 61.7 | 81.7 |
| 6a | Sn-Beta/HCl (pH = 2) | $H_2O$ | 110 | 0 | 0 | — |
| 6b | Sn-Beta/HCl (pH = 2) | $H_2O$ | 110 | 15 | 25 | 95 |
| 6c | Sn-Beta/HCl (pH = 2) | $H_2O$ | 110 | 45 | 45.6 | 95 |
| 6d | Sn-Beta/HCl (pH = 2) | $H_2O$ | 110 | 90 | 62 | 77.9 |
| 7a | — | $H_2O$ | 140 | 0 | 0 | — |
| 7b | — | $H_2O$ | 140 | 90 | 5.5 | 9 |
| 8a | HCl (pH = 2) | $H_2O$ | 140 | 0 | 0 | — |
| 8b | HCl (pH = 2) | $H_2O$ | 140 | 90 | 7 | 6.3 |
| 9a | Ti-Beta | $H_2O$ | 140 | 0 | 0 | — |
| 9b | Ti-Beta | $H_2O$ | 140 | 15 | 35.3 | 65 |
| 9c | Ti-Beta | $H_2O$ | 140 | 45 | 44.1 | 68.3 |
| 9d | Ti-Beta | $H_2O$ | 140 | 60 | 47.5 | 67.1 |
| 10a | Sn-Beta | $H_2O$ | 140 | 0 | 0 | — |
| 10b | Sn-Beta | $H_2O$ | 140 | 5 | 32.3 | 98 |
| 10c | Sn-Beta | $H_2O$ | 140 | 10 | 43.4 | 96.9 |
| 10d | Sn-Beta | $H_2O$ | 140 | 15 | 51.1 | 95.1 |
| 10e | Sn-Beta | $H_2O$ | 140 | 30 | 72.3 | 70.1 |
| 11a | — | DMSO | 140 | 0 | 0 | — |
| 11b | — | DMSO | 140 | 15 | 11.4 | 0 |
| 11c | — | DMSO | 140 | 45 | 67.9 | 0 |
| 11d | — | DMSO | 140 | 150 | 81 | 0 |
| 12a | HCl (pH = 2) | DMSO | 140 | 0 | 0 | — |
| 12b | HCl (pH = 2) | DMSO | 140 | 15 | 71.7 | 0 |
| 12c | HCl (pH = 2) | DMSO | 140 | 45 | 77.3 | 0 |
| 13a | Sn-Beta | DMSO | 140 | 0 | 0 | — |
| 13b | Sn-Beta | DMSO | 140 | 15 | 16.6 | 0 |
| 13c | Sn-Beta | DMSO | 140 | 45 | 67.2 | 0 |
| 13d | Sn-Beta | DMSO | 140 | 150 | 81.6 | 0 |
| 14a | Sn-Beta/HCl (pH = 2) | DMSO | 140 | 0 | 0 | — |
| 14b | Sn-Beta/HCl (pH = 2) | DMSO | 140 | 15 | 69.3 | 0 |
| 14c | Sn-Beta/HCl (pH = 2) | DMSO | 140 | 45 | 77.6 | 0 |

Figure 23:
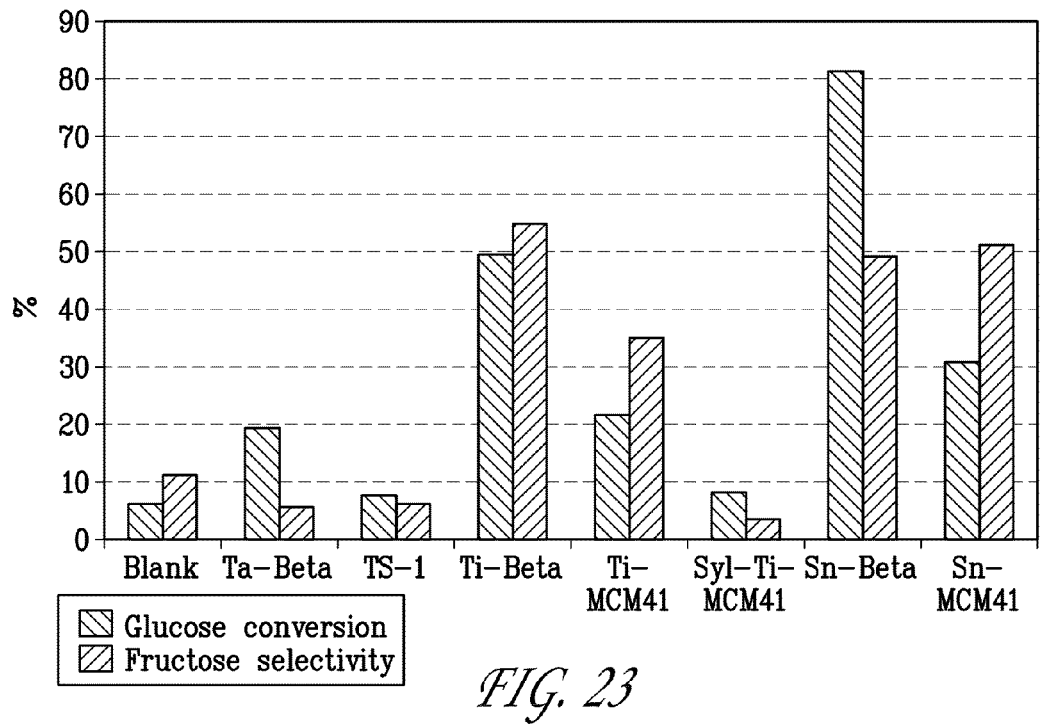
FIG. 23 depicts the results of a screening of metallosilicates for the glucose isomerization reaction. The reaction conditions were 10 wt % glucose in water, 140° C., 90 min, and 1:50 metal:glucose molar ratio.

A series of materials containing different Lewis acid centers for their activity on the glucose isomerization reaction was examined. The tests included tantalum (Ta), tin (Sn), and titanium (Ti) metal centers incorporated into the framework of a large-pore Beta zeolite, Ti into a medium-pore zeolite (TS-1) and Sn and Ti into an ordered mesoporous siliceous support (SBA-15). As seen in FIG. 23, Sn-Beta and Ti-Beta showed the highest isomerization activity under these conditions, reaching glucose conversions above 50% in 90 minutes at 140° C. In contrast, Sn-SBA and Ti-SBA only showed moderate isomerization activity under these conditions, TS-1 and Ta-Beta materials showed little isomerization activity, under the same reaction conditions. Reactivity differences between TS-1 and Ti-Beta suggest that the diameter of the TS-1 pores are too small to allow the entrance of glucose molecules into the zeolite.

A more detailed study of the reaction kinetics of the two most active materials showed that the Sn-Beta catalyst isomerizes glucose with superior performance when compared to Ti-Beta. Specifically, fructose selectivities exceeding 90% were achieved at reaction equilibrium (i.e. 50% glucose conversion) in 45 min at 110° C. and in 15 min at 140° C. Fructose selectivity values decreased when the reaction was allowed to proceed for longer times, due to the onset of fructose degradation reactions (see entries 5d and 10e). The Ti-Beta catalyst, while active, was not as effective in these conditions as the Sn-Beta catalyst, generating after 45 min at 110° C., a fructose selectivity of 80% at 18% glucose conversion, and after 45 min at 140° C. a fructose selectivity of 68% at a 44% glucose conversion.

We observed interesting solvent effects related to the activity of Sn-Beta on the isomerization reaction. Unlike basic catalysts, the Sn-Beta catalyst was able to perform the isomerization reaction in an acidic environment. Indeed, a main drawback of basic catalysts used for this reaction is catalyst deactivation due to neutralization of active sites by carboxylic acids formed during sugar degradation reactions. However, when Sn-Beta was used in an acidic glucose solution (pH=2, HCl), no difference in activity or in fructose selectivity was observed when compared to the reaction performed in the non-acidic solution (see entries 5c and 6c). In contrast, when an aprotic solvent (dimethylsulfoxide [DMSO]) was used instead of water, the Sn-Beta was not active for the isomerization reaction (see entries 11c and 12c).

Example 9

The following table summarizes glucose isomerization experiments using various catalysts in water. Reactions were performed with a 10 wt % glucose solution, using the corresponding amount of catalyst to maintain a 1:50 metal:glucose molar ratio, with the exception of entry 10, indicated by *, which reports the results of a reaction of a 45 wt % glucose solution, using a 225:1 glucose:Sn molar ratio. The ** indicates that an unidentified sugar, rather than mannose, was obtained with Ti-Beta. The reported 5 wt % yield was calculated using the response factor associated with hexoses.

product yields of approximately 46% (w/w) glucose, 31% (w/w) fructose, and 9% (w/w) mannose after 30 min and 12 min at 383 K and 413 K, respectively. At the 383 K, the Ti-Beta catalyst achieved much lower glucose conversions, even when the reaction was allowed to proceed for longer periods of time (entries 4 and 7). The onset of auto-catalyzed degradation reactions decreased total saccharide yields with increased reaction times (FIGS. 25-30). Varying the reaction temperature did not appear to have an impact on the total amount of sugar lost at a given glucose conversion value, thus suggesting that the degradation reaction pathway has an apparent activation barrier similar to that of the isomerization reaction. Notably, the Sn-Beta catalyst can be used with more concentrated glucose solutions like those employed in large-scale conversion. For example, a product distribution of 46% (w/w) glucose, 29% (w/w) fructose, and 8% (w/w) mannose was obtained after reacting a 45 wt % glucose solution containing a catalytic amount of Sn-Beta (1:225 Sn:glucose molar ratio) for 60 min at 383 K (entries 4 and 10). This result approximates those obtained in the industrial enzymatic process, and is a high fructose yield obtained from a highly concentrated glucose solution using an inorganic catalyst.

Figure 12:
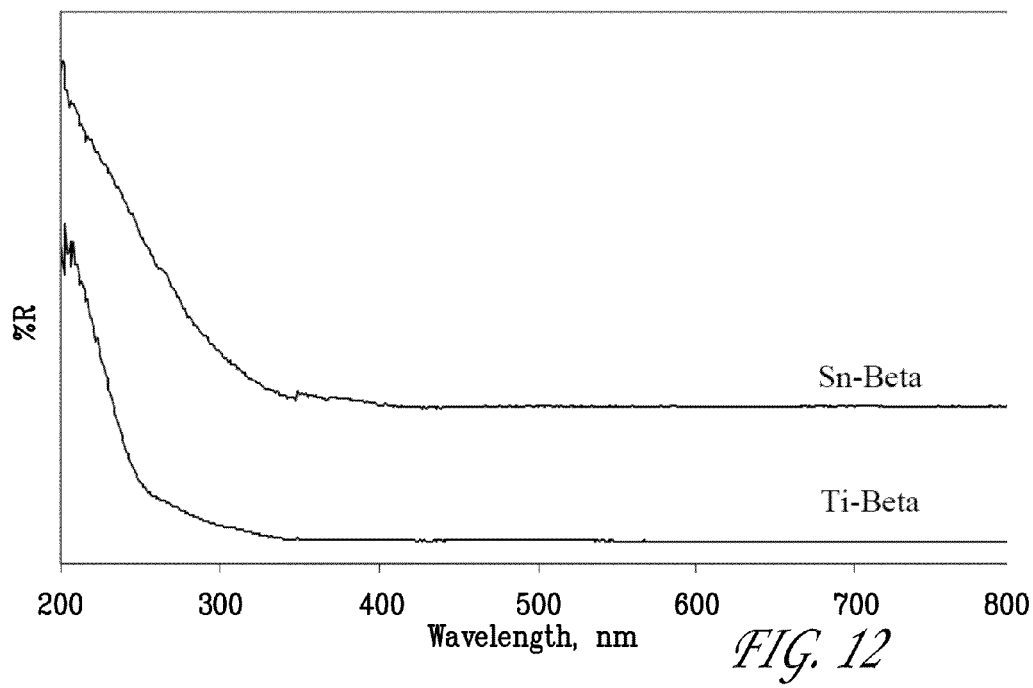
FIG. 12 depicts ultraviolet/visible diffuse reflectance spectra of Sn-Beta and Ti-Beta.
Figure 13:
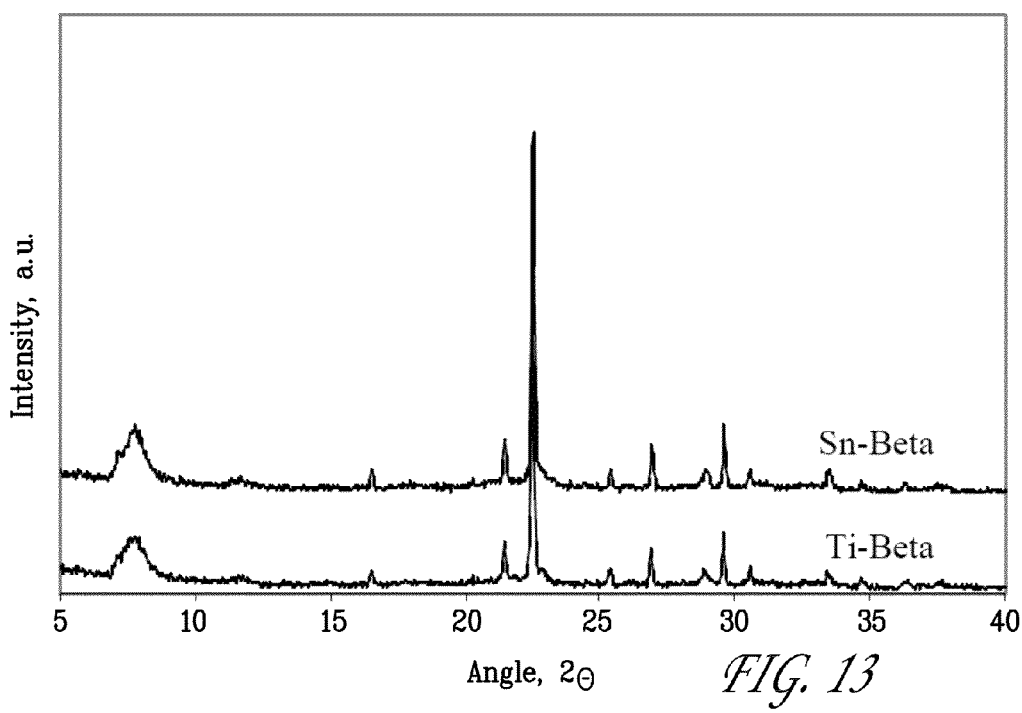
FIG. 13 depicts X-ray powder diffraction patterns of Ti-Beta and Sn-Beta.
Figure 14:
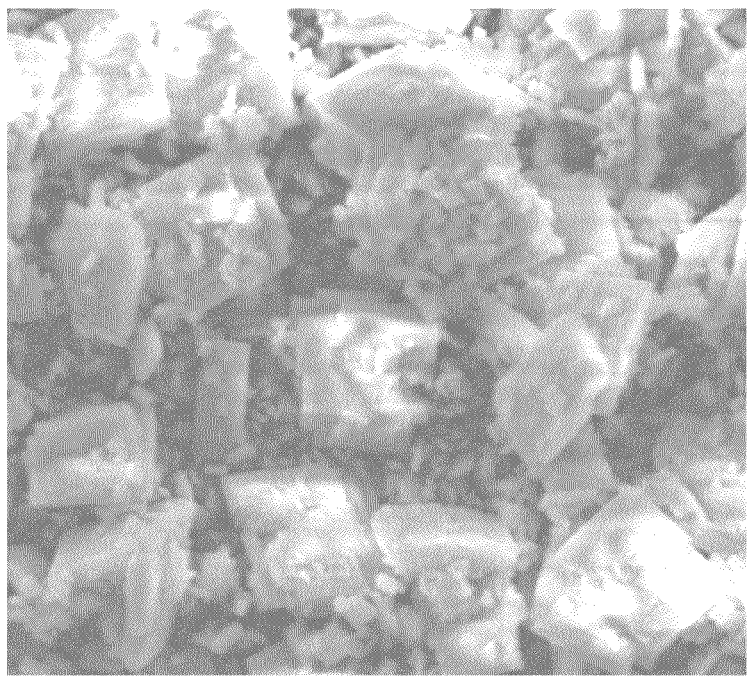
FIGS. 14-15 depict the absence of significant morphological changes of Sn-Beta using scanning electron microscopy after the conversion of glucose to HMF in a biphasic system.
Figure 15:
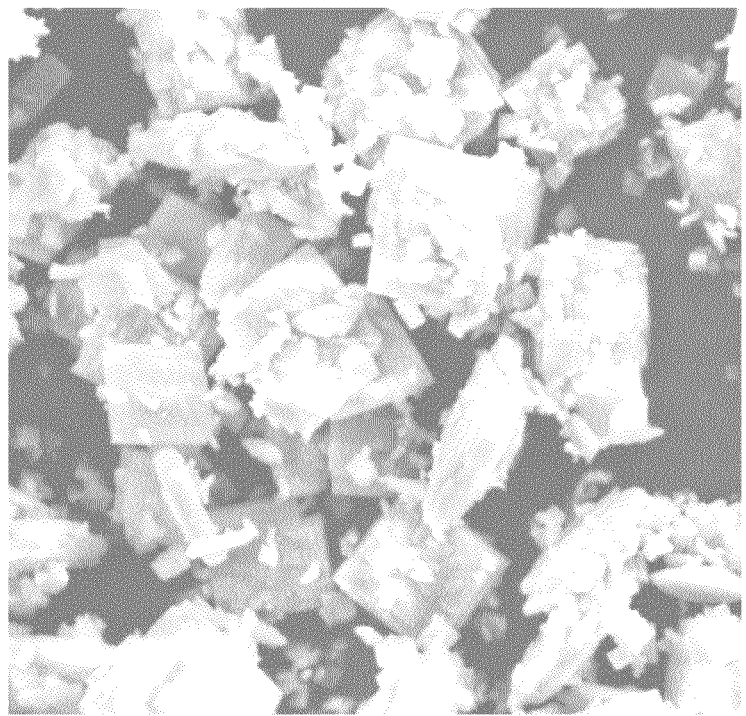
Figure 16:
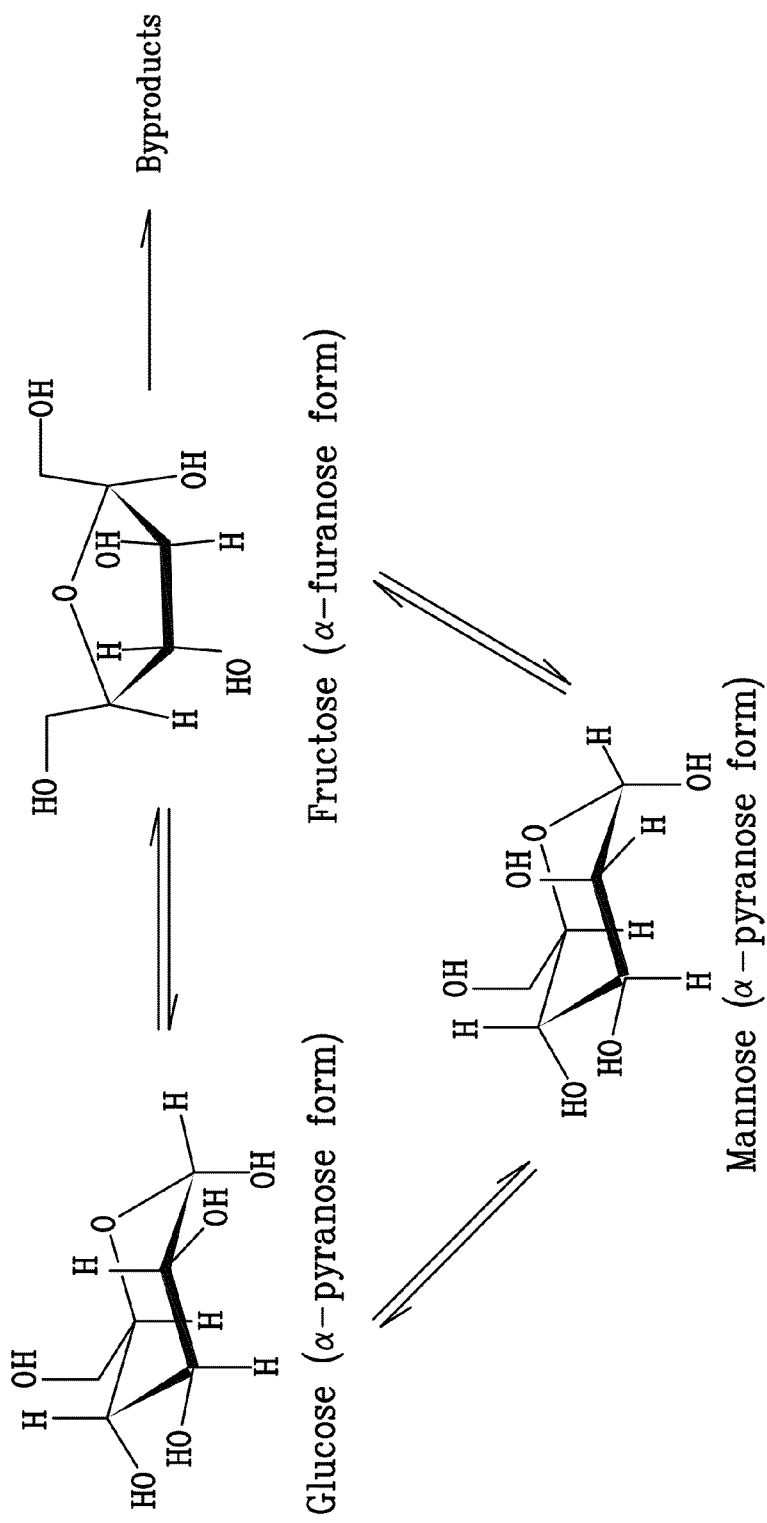
FIG. 16 depicts a schematic representation of the glucose isomerization reaction pathways catalyzed by either biological or chemical catalysts.
Figure 17:
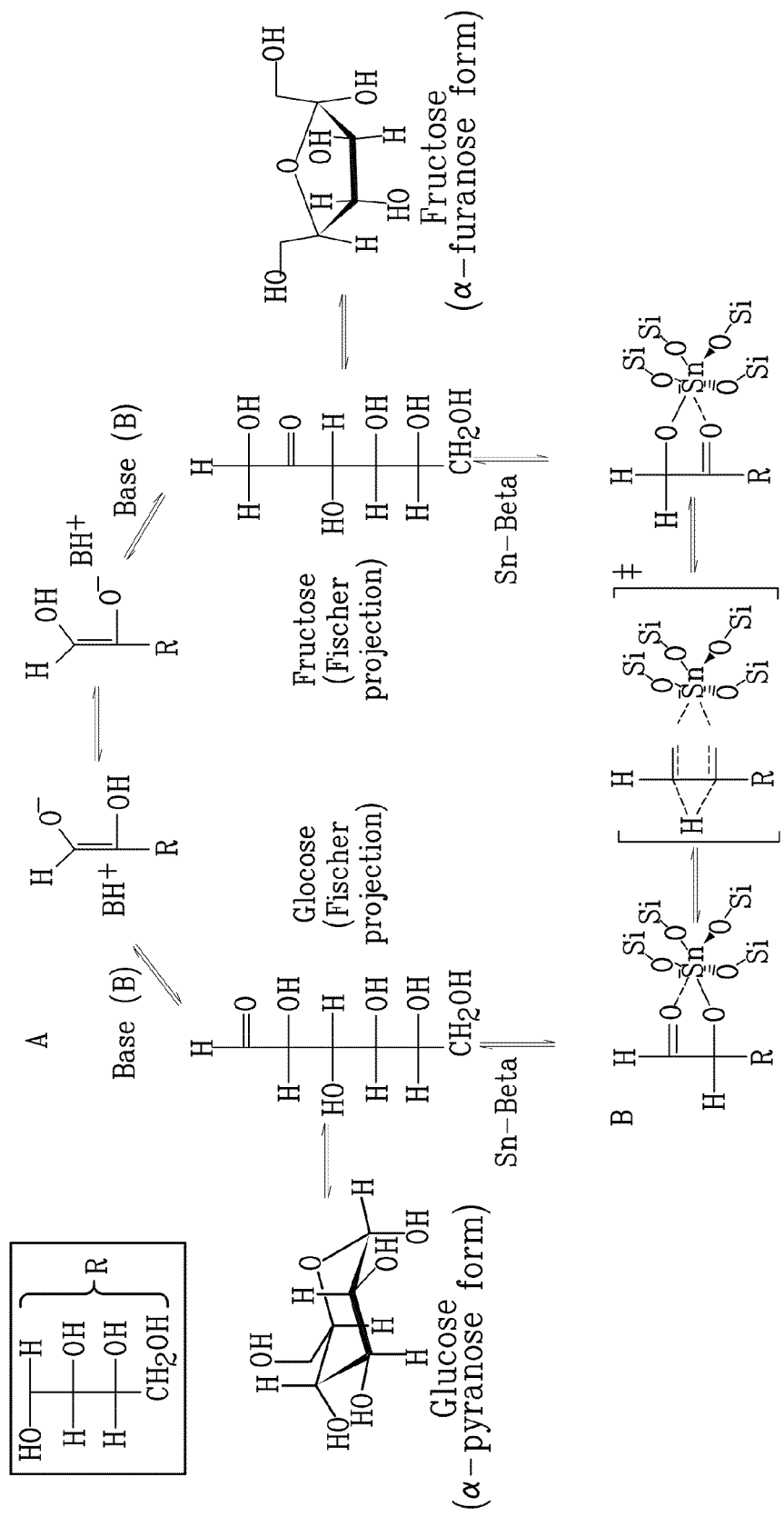
FIG. 17 depicts a schematic representation of the glucose isomerization mechanisms by way of (A) base-catalyzed and (B) metal-catalyzed reaction pathways.
Figure 19:
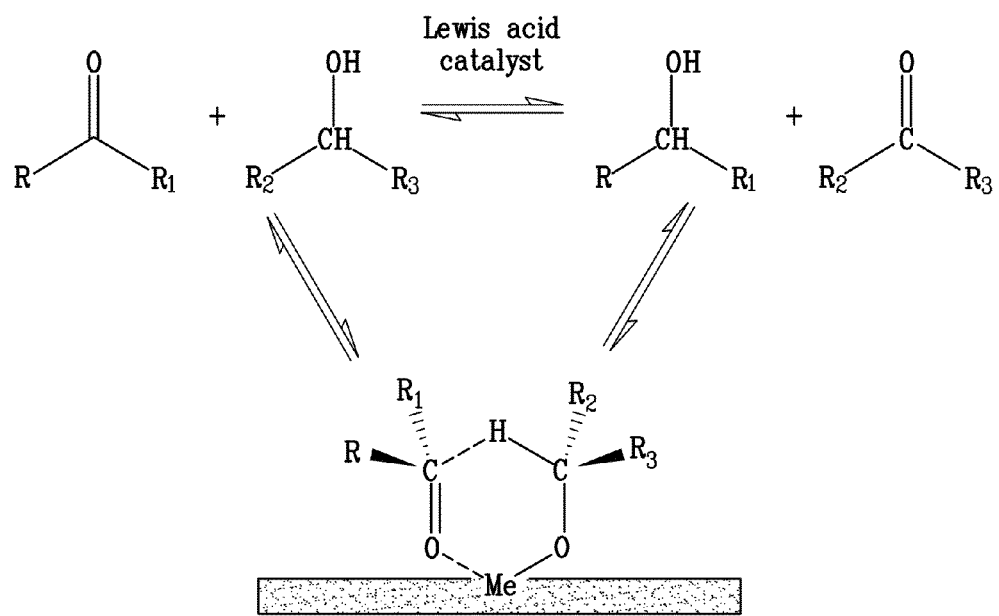
FIG. 19 depicts the Meerwein-Ponndorf-Verley (MPV) reaction pathway. R=alkyl or aryl; R1 and R3=alkyl or hydrogen; Me=metal.
Figure 20:
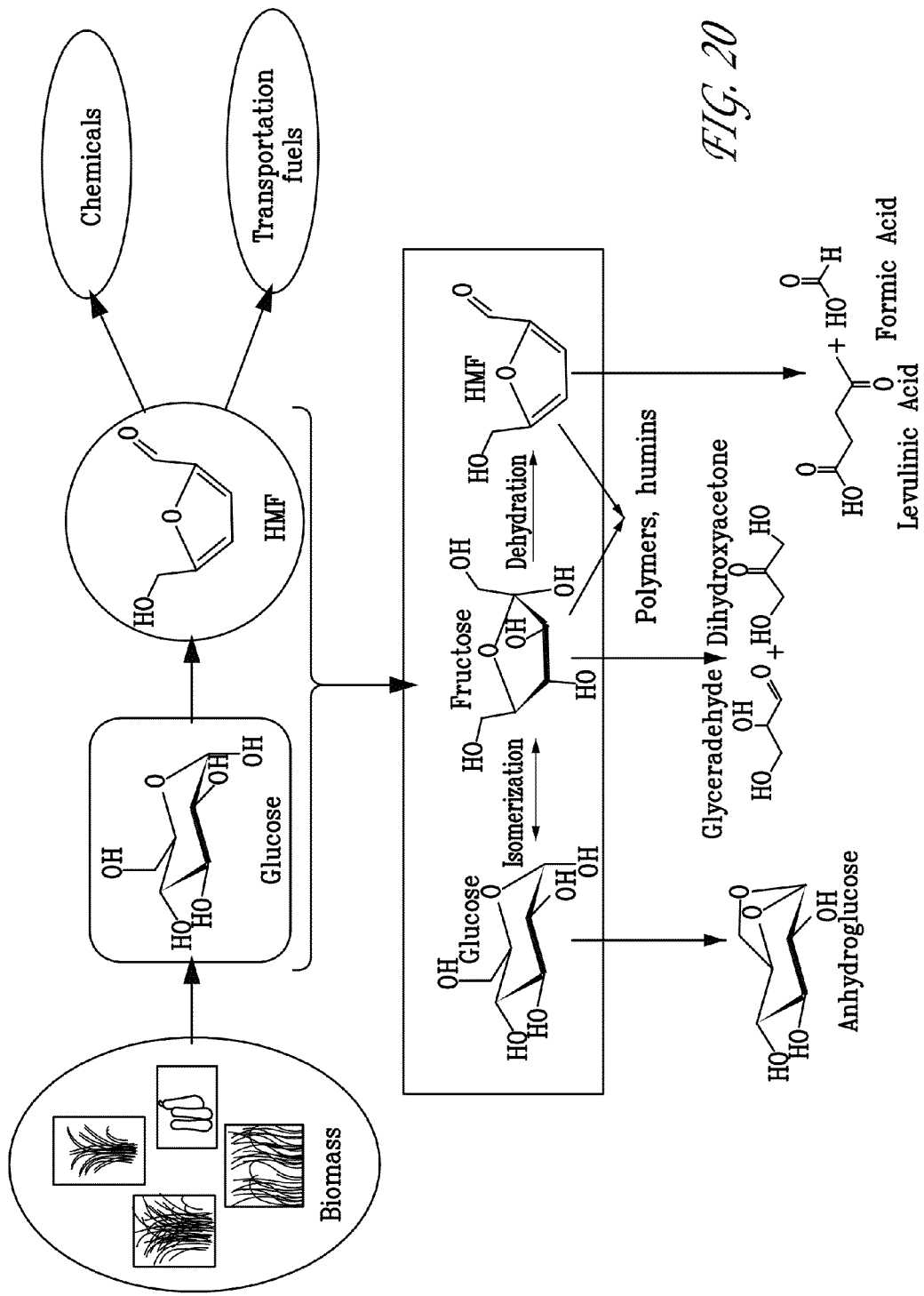
FIG. 20 depicts a schematic representation of the pathway from biomass to glucose to HMF to fructose to downstream products.
Figure 21:
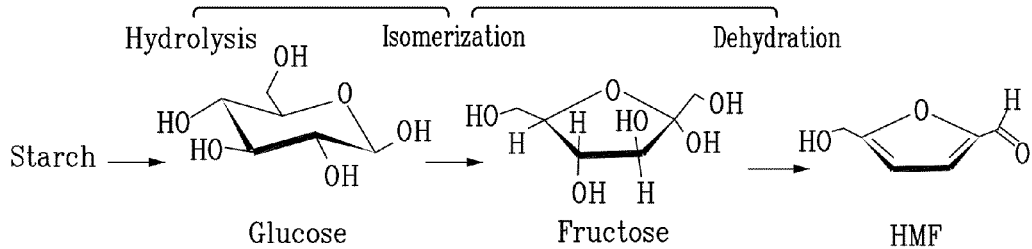
FIG. 21 depicts a schematic representation of the pathway from starch to glucose to fructose to HMF.
Figure 22:
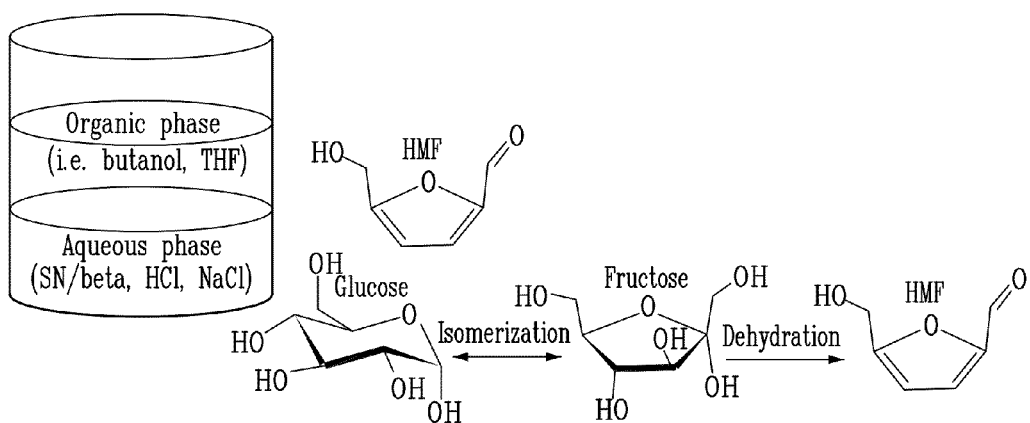
FIG. 22 depicts a schematic representation of the use of a biphasic system for the reaction of glucose to form fructose to form HMF.

The data suggest that the active sites for the isomerization reaction in Sn-Beta are Sn atoms incorporated into the framework of the zeolite. Neither $SnCl_4 \cdot 5H_2O$ or $SnO_2$ showed isomerization activity (entries 8 and 9), and UV data for Sn-Beta did not reveal absorption bands corresponding to extra-framework Sn (FIG. 12).

| Entry | Catalyst | Temp. (K.) | Time (min) | Glucose | Fructose | Mannose | Total Saccharides |
|---|---|---|---|---|---|---|---|
| 1 | None | 383 | 90 | 97 | 0 | 0 | 97 |
| 2 | None | 413 | 90 | 95 | 1 | 0 | 95 |
| 3 | HCl (pH = 2) | 383 | 90 | 98 | 0 | 0 | 98 |
| 4 | Sn-Beta | 383 | 30 | 45 | 32 | 9 | 86 |
| 5 | Sn-Beta | 413 | 12 | 46 | 30 | 9 | 85 |
| 6 | Sn-Beta/HCl (pH = 2) | 383 | 30 | 44 | 33 | 9 | 86 |
| 7 | Ti-Beta | 383 | 90 | 74 | 14 | 5** | 93 |
| 8 | $SnO_2$ | 383 | 60 | 96 | 0 | 0 | 96 |
| 9 | $SnCl_4 \cdot 5H_2O$ | 383 | 60 | 90 | 0 | 0 | 90 |
| 10* | Sn-Beta | 383 | 60 | 46 | 29 | 8 | 83 |

Figure 24:
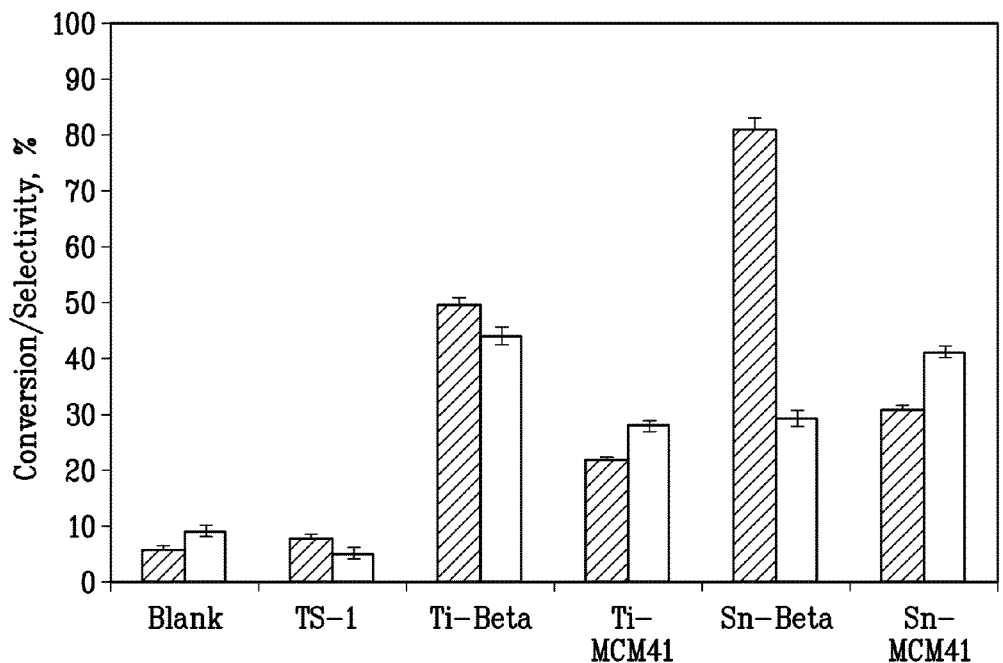
FIG. 24 depicts the results of the glucose isomerization reaction catalyzed by various metal containing solids (Glucose conversion in stripes, Fructose selectivity in white). Reaction conditions were 10 wt % glucose in water, 413 K, 90 min, and 1:50 metal:glucose molar ratio.
Figure 25:
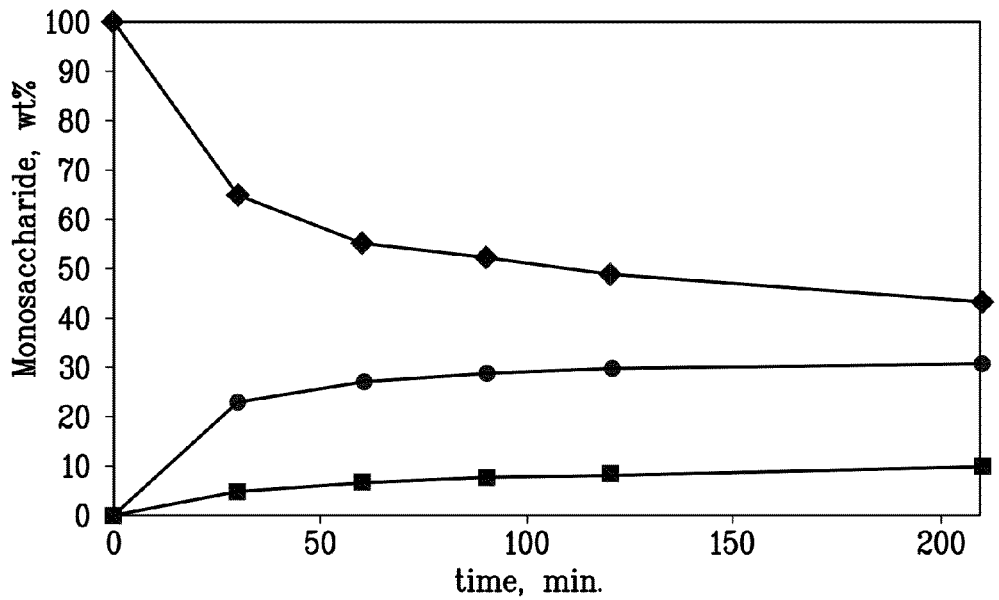
FIGS. 25-30 depict glucose isomerization reaction profiles and product distributions as a function of time at 363 K, 383 K, and 413 K for Glucose (stripes from lower left to upper right), Fructose (white), and Mannose (stripes from upper left to lower right) using Sn-Beta as a catalyst. Reaction conditions were 10 wt % glucose in water and 1:50 Sn:glucose molar ratio. The error bars for the reaction profile plots on FIGS. 25, 27, and 29 are not visible because they are smaller than the data-point icons.
Figure 26:
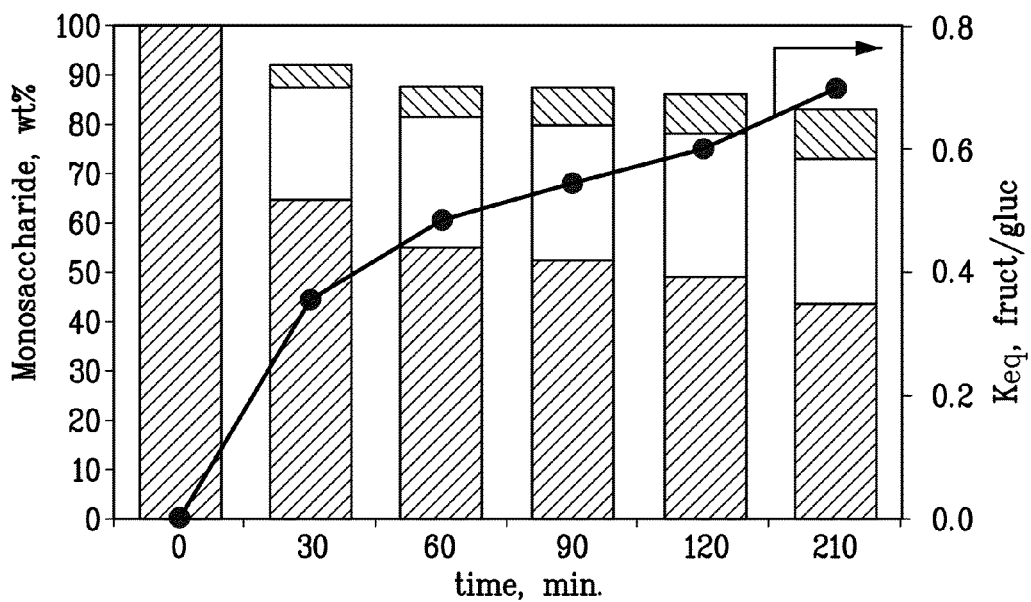
Figure 27:
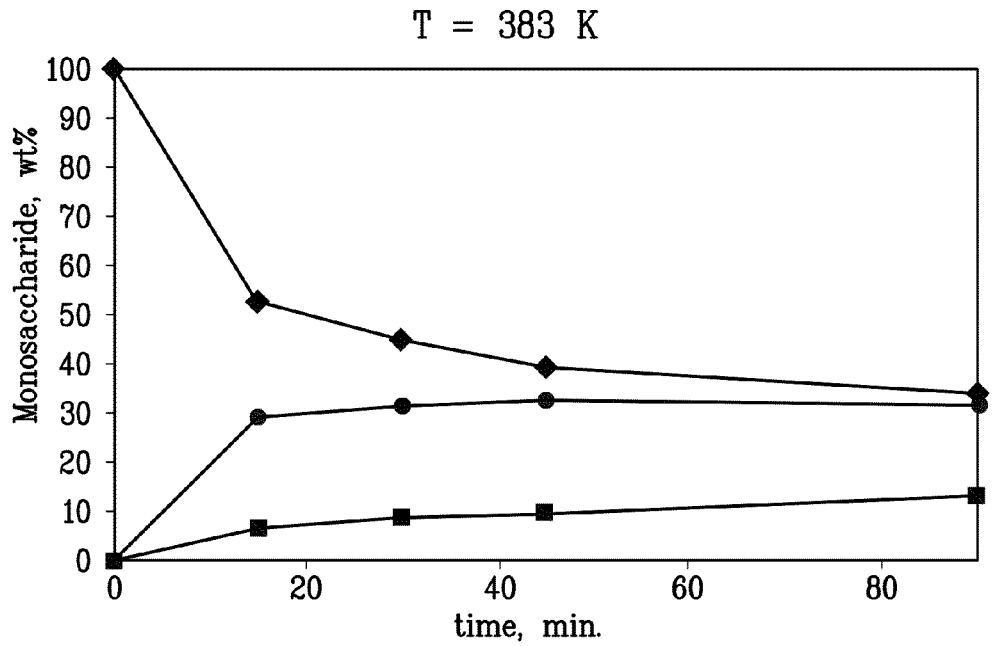
Figure 28:
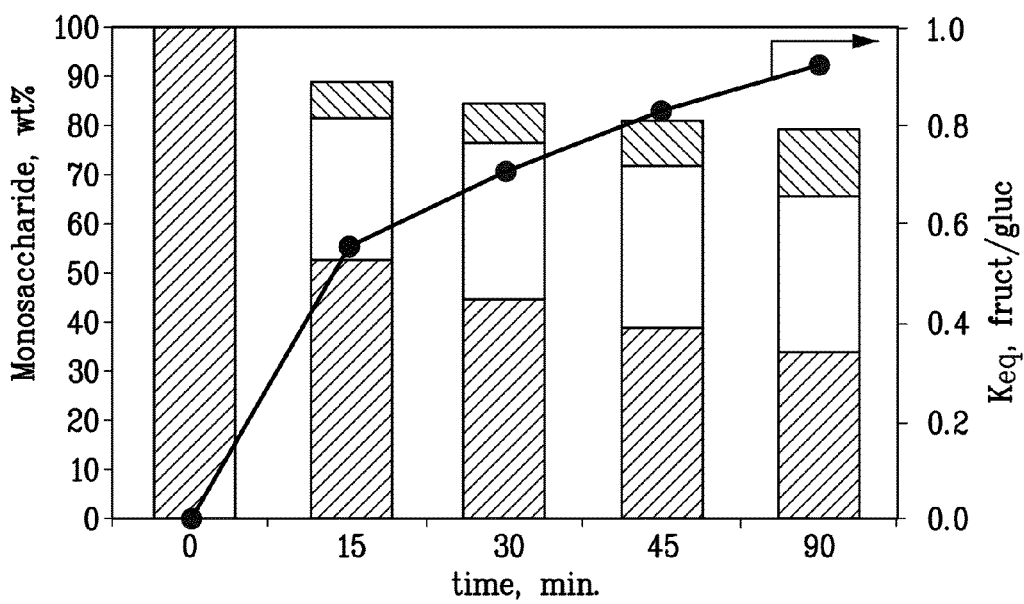
Figure 29:
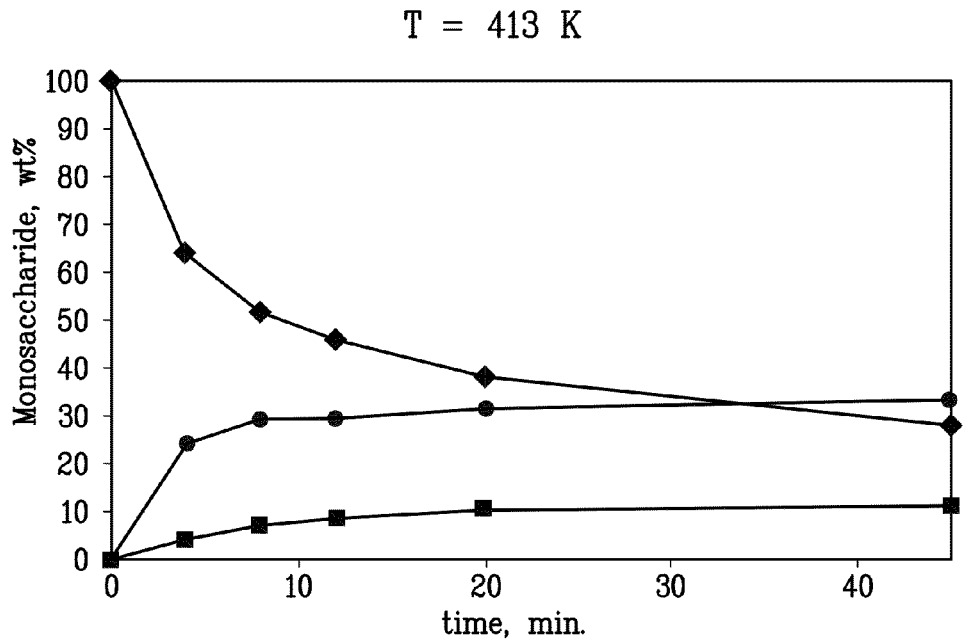
Figure 30:
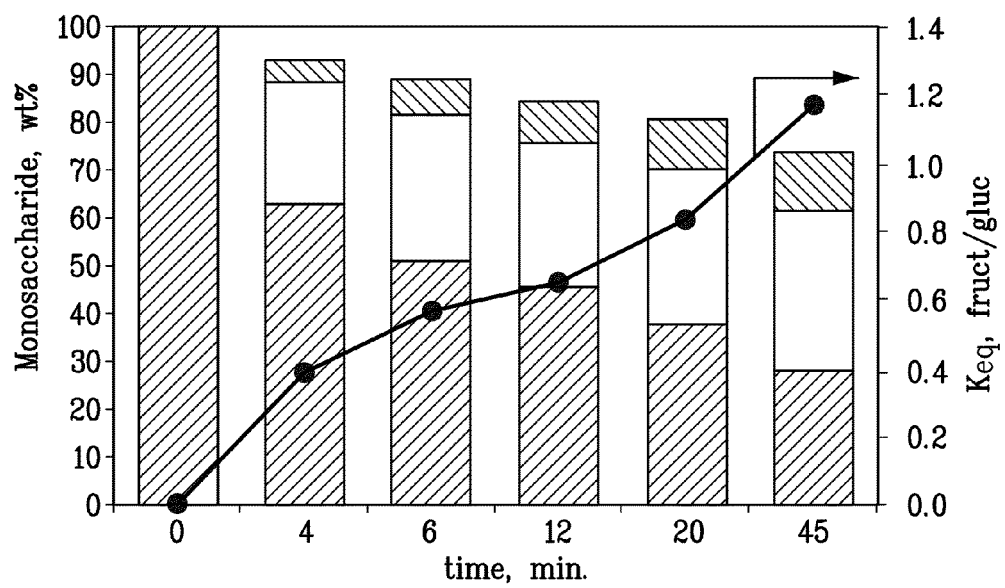

A series of silica materials containing either Sn or Ti metal centers were screened for their activity in the glucose isomerization reaction. Specifically, Sn and Ti metal centers were incorporated into the framework of a large-pore zeolite (Beta), Ti was incorporated into a medium-pore zeolite (TS-1), and Sn and Ti were incorporated into an ordered mesoporous silica (MCM-41). Under these conditions, Sn-Beta and Ti-Beta showed the highest glucose isomerization activity, reaching glucose conversions above 50% in 90 min at 413 K (FIG. 24). In contrast, Sn-MCM41 and Ti-MCM41 only revealed moderate activity, and TS-1 was virtually inactive under the same reaction conditions (FIG. 24). Reactivity differences between TS-1 and Ti-Beta indicate that glucose molecules are able to diffuse into the pores of the Beta zeolite (ca. 0.8 nm pore diameter), but not into the pores of TS-1 (0.5-0.6 nm pore diameter).

Further reaction studies with the two most active materials showed that the Sn-Beta catalyst isomerizes glucose with superior performance when compared to Ti-Beta. Specifically, a 10 wt % glucose solution containing a catalytic amount of Sn-Beta (1:50 Sn:glucose molar ratio) generated Example 10

The following table summarizes results for catalyst stability studies. Reactions were performed at 383 K using a 10 wt % glucose solution with a 1:50 Sn:glucose molar ratio (except for entry 5b). For Study 1 (entries 1-4), after each cycle, the catalyst was washed with water and fresh glucose solution was subsequently added to start a new cycle. In Cycle 4, the catalyst recovered from Cycle 3 was calcined in air at 813 K for 3 h using a temperature ramp rate of 2 K/min. For Study 2 (entries 5a-5b), the reaction with Sn-Beta was allowed to proceed for 12 min (entry 5a). Then, the catalyst was filtered hot from the solution, and the filtrate was reacted for an additional 30 min (entry 5b).

| Entry | Catalyst | Time (min) | Glucose | Fructose | Mannose |
|---|---|---|---|---|---|
| 1 | Sn-Beta Cycle 1 | 30 | 41 | 32 | 9 |
| 2 | Sn-Beta Cycle 2 | 30 | 45 | 30 | 8 |

| Entry | Catalyst | Time (min) | Glucose | Fructose | Mannose |
|---|---|---|---|---|---|
| 3 | Sn-Beta Cycle 3 | 30 | 47 | 29 | 7 |
| 4 | Sn-Beta Cycle 4 (calcination) | 30 | 46 | 30 | 8 |
| 5a | Sn-Beta | 12 | 57 | 27 | 6 |
| 5b | None (catalyst removed by filtration) | 30 | 57 | 27 | 6 |

To test the stability of the Sn-Beta catalyst, two types of studies were performed. In the first study, the reusability of the catalyst was tested by performing four consecutive isomerization cycles at 383 K for 30 min each. After each cycle, the catalyst was filtered and washed with water before adding a fresh glucose solution. As seen from the data, after three reaction cycles, the catalyst maintained its initial activity and product distribution. After the third cycle, the catalyst was calcined in air at 813 K before performing one last cycle. The cycle 4 results show that the catalyst again maintained its original activity and product distribution thereby confirming that it is able to withstand a typical zeolite regeneration process. A second test was designed to probe for the presence of homogeneous catalysis due metal species leached into the solution. Specifically, an isomerization cycle was initiated with the Sn-Beta catalyst at 383 K for 15 min. The catalyst was then removed by filtration while the solution was still hot. In order to avoid any possible re-adsorption of leached species during cool-down, and the filtrate was allowed to react at 383 K for 30 min. The reaction results show that in the presence of catalyst, glucose isomerization proceeded as expected (product yields of 57% (w/w) glucose, 27% (w/w) fructose, and 6% (w/w) mannose). However, the reaction did not continue once the catalyst was removed indicating that no homogenous catalysis occurred by leached metal ions (entries 5a and 5b). The results from these two tests indicate that Sn-Beta is heterogeneously catalyzing the isomerization reaction and can be used for multiple reaction cycles.

Example 11

The following table summarizes results for Sn-catalyzed glucose reactions in water under acidic conditions at 413 K. For entries 1b and 4, a 1:50 Sn:glucose molar ratio was used.

| Entry | Feed Solution | Catalyst | Time (min) | Starch | Glucose | Fructose | Mannose | HMF |
|---|---|---|---|---|---|---|---|---|
| 1a | 10 wt % starch | HCl (pH = 1) | 90 | 13 | 87 | 0 | 0 | 0 |
| 1b | post-reaction mixture of entry 1a | Sn-Beta + HCl (pH = 1) | 12 | 13 | 39 | 23 | 7 | 0 |
| 2 | 10 wt % glucose | HCl (pH = 1) | 120 | — | 91 | 0 | 0 | 1 |
| 3 | 10 wt % fructose | HCl (pH = 1) | 120 | — | 0 | 15 | 0 | 24 |
| 4 | 10 wt % glucose | Sn-Beta + HCl (pH = 1) | 120 | — | 28 | 18 | 2 | 11 |

Remarkably, Sn-Beta is able to perform the isomerization reaction in a highly acidic environment. No differences in activity or product distribution were observed for reactions using Sn-Beta in an acidic 10 wt % glucose solution (pH=2, HCl), when compared to the reaction performed without HCl (Example 9, entries 4 and 6). Experiments using Sn-Beta in an acidic environment showed good results for hydrolysis/isomerization and isomerization/dehydration reaction sequences. Specifically, hydrolysis of a 10 wt % starch solution using HCl (pH=1) at 413 K for 90 min generated a 87% (w/w) glucose and 13% (w/w) starch solution that was then isomerized by adding a catalytic amount of Sn-Beta (1:50 Sn:glucose molar ratio) to the acidic solution and heating for an additional 12 min at 413 K to obtain a product distribution consisting of 13% (w/w) starch, 39% (w/w) glucose, 23% (w/w) fructose, and 7% (w/w) mannose (Table 3, entries 1a and 1b). Also, a 10 wt % glucose solution reacted in the presence of HCl (pH=1) and Sn-Beta together for 120 min at 413 K generated an HMF yield of 11% (w/w) in addition to 18% (w/w) fructose and 2% (w/w) mannose (entry 4). These data can be compared to the dehydration results obtained from reacting fructose in aqueous HCl (24% (w/w) HMF yield, 85% conversion; entry 3) and from dehydrating glucose under similar aqueous HCl reaction conditions (<1% (w/w) HMF yield, 9% conversion; entry 2). Thus, Sn-Beta is an attractive candidate for one-pot reaction sequences requiring catalytic couplings of isomerization and other acid catalyzed reactions.

Example 12

Figure 34:
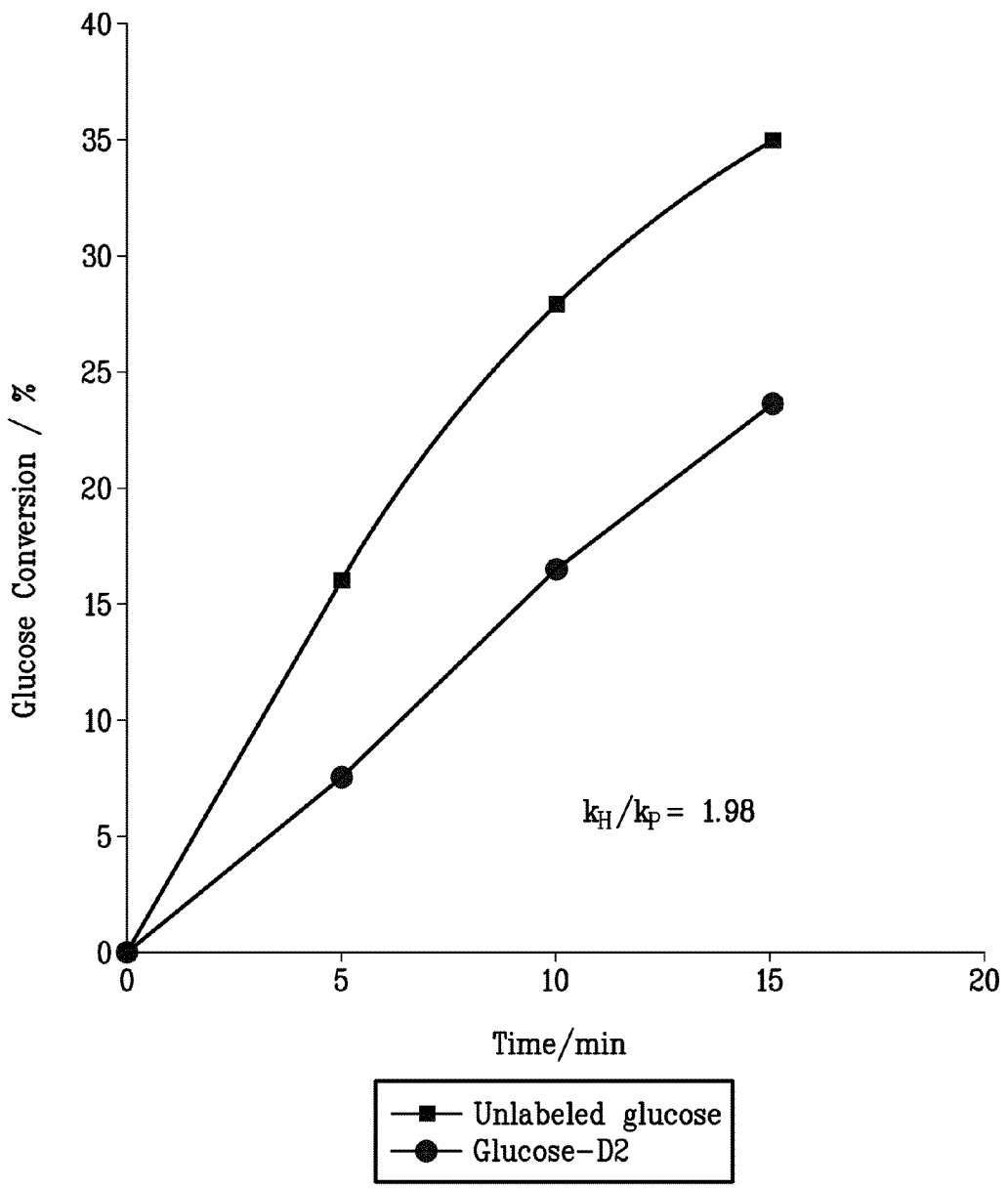
FIG. 34 depicts glucose isomerization conversion profiles at 383 K, using Sn-Beta as a catalyst. Reaction conditions were 10 wt % glucose (unlabeled or labeled) in water and 1:50 Sn:glucose molar ratio.
Figure 35A:
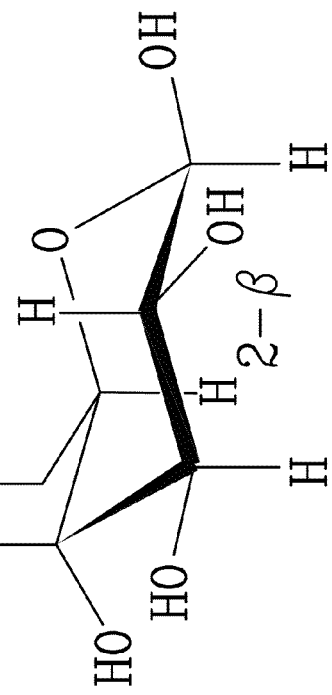
FIG. 35 depicts molecular structures for an unlabeled glucose solution containing 35% glucose in the α-pyranose configuration (A) and 65% in the β-pyranose configuration (B). The same ratios are obtained for labeled glucose (glucose-D2), where 35% is in the α-pyranose configuration (C) and 65% is in the β-pyranose configuration (D).
Figure 35B:
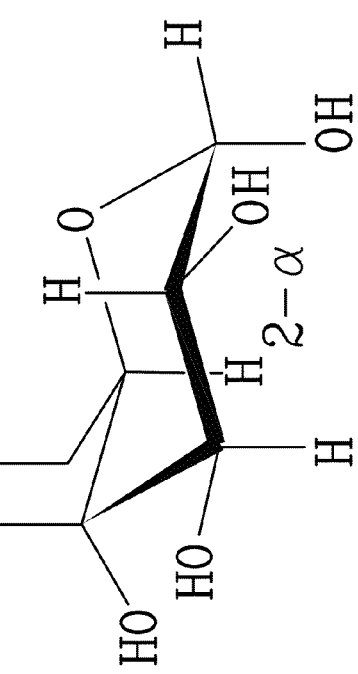
Figure 35C:
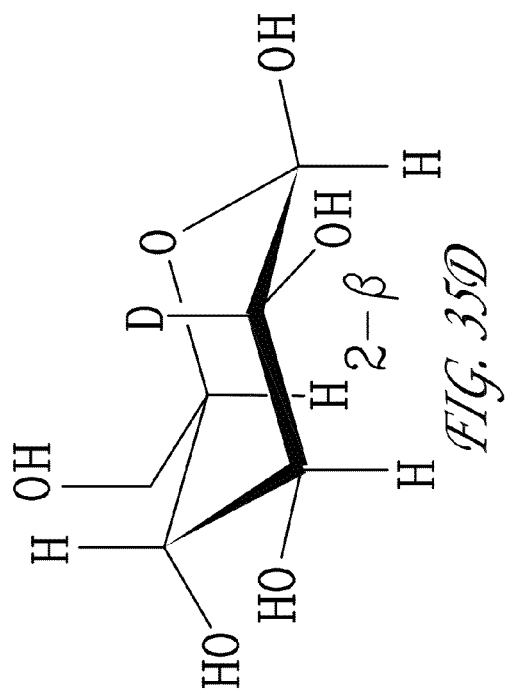
Figure 35D:
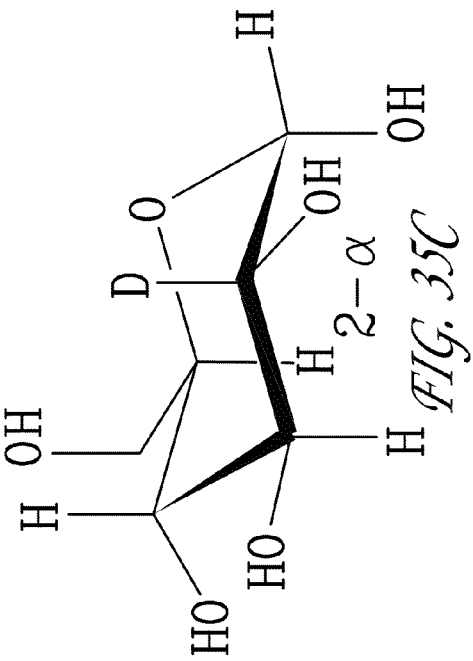
Figure 36:
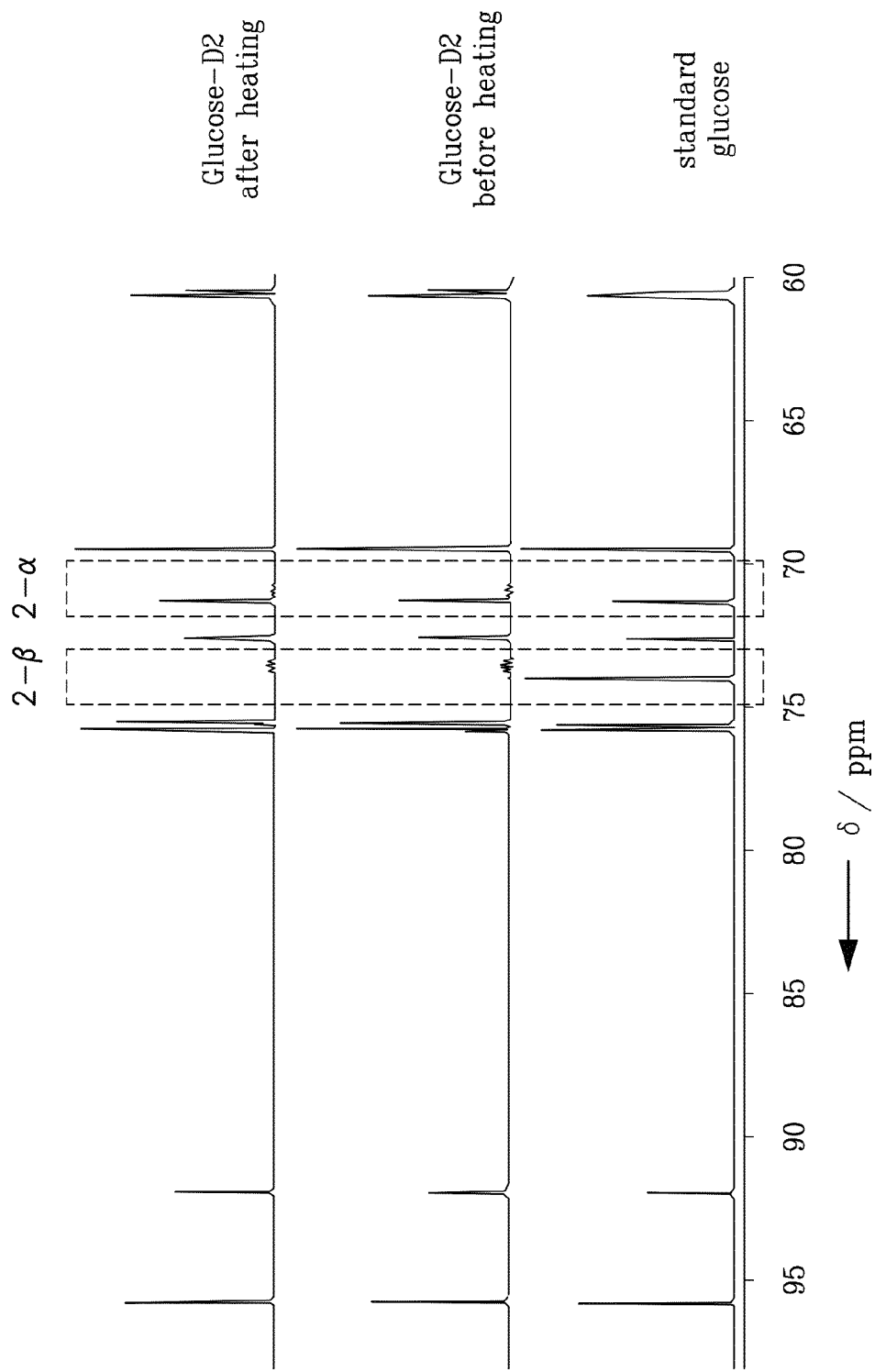
FIGS. 36-37 depict $^{13}$C NMR spectra of unlabeled glucose, glucose-D2 before heating, and glucose-D2 after heating at 383 K without a catalyst.
Figure 37:
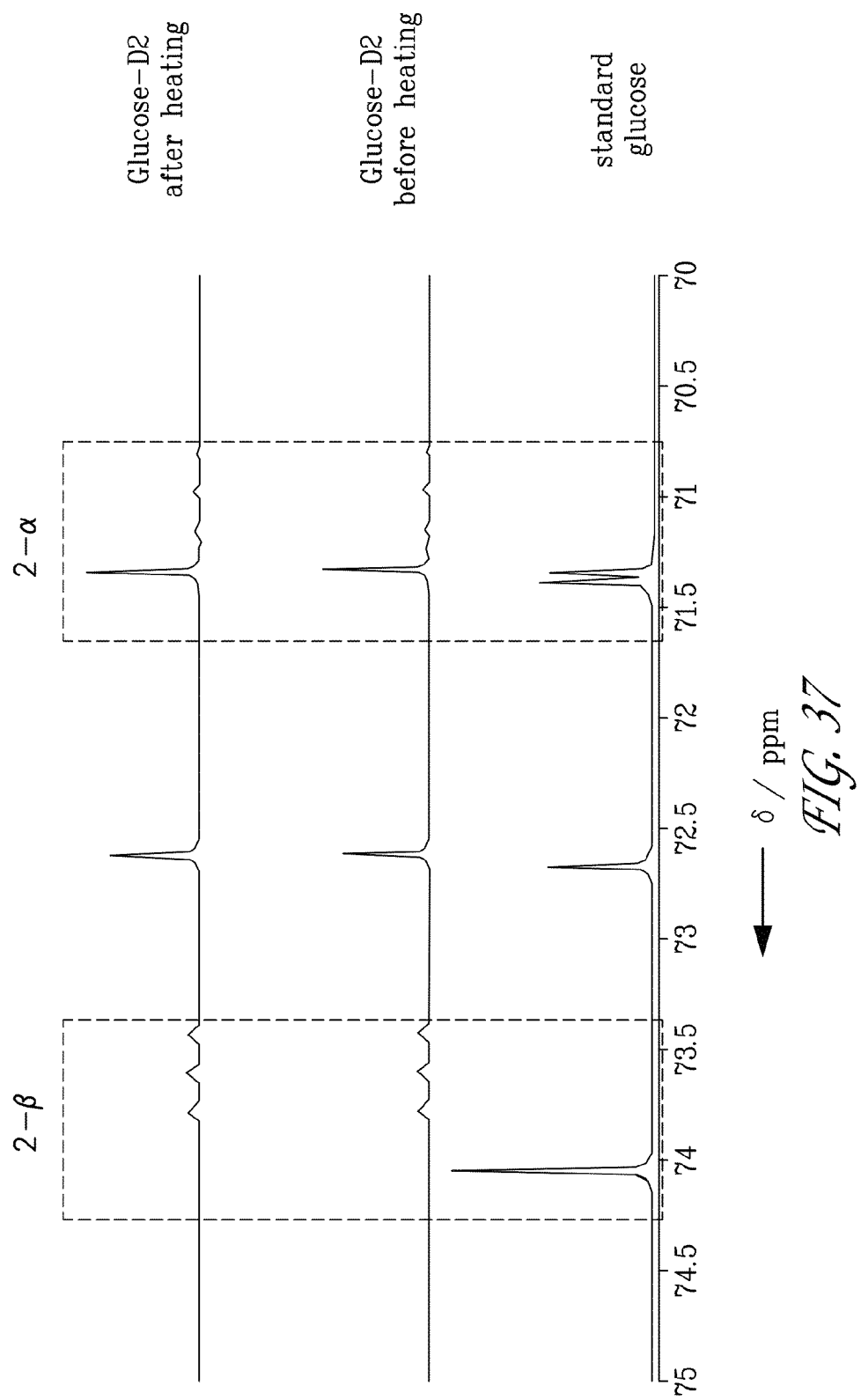
Figure 38:
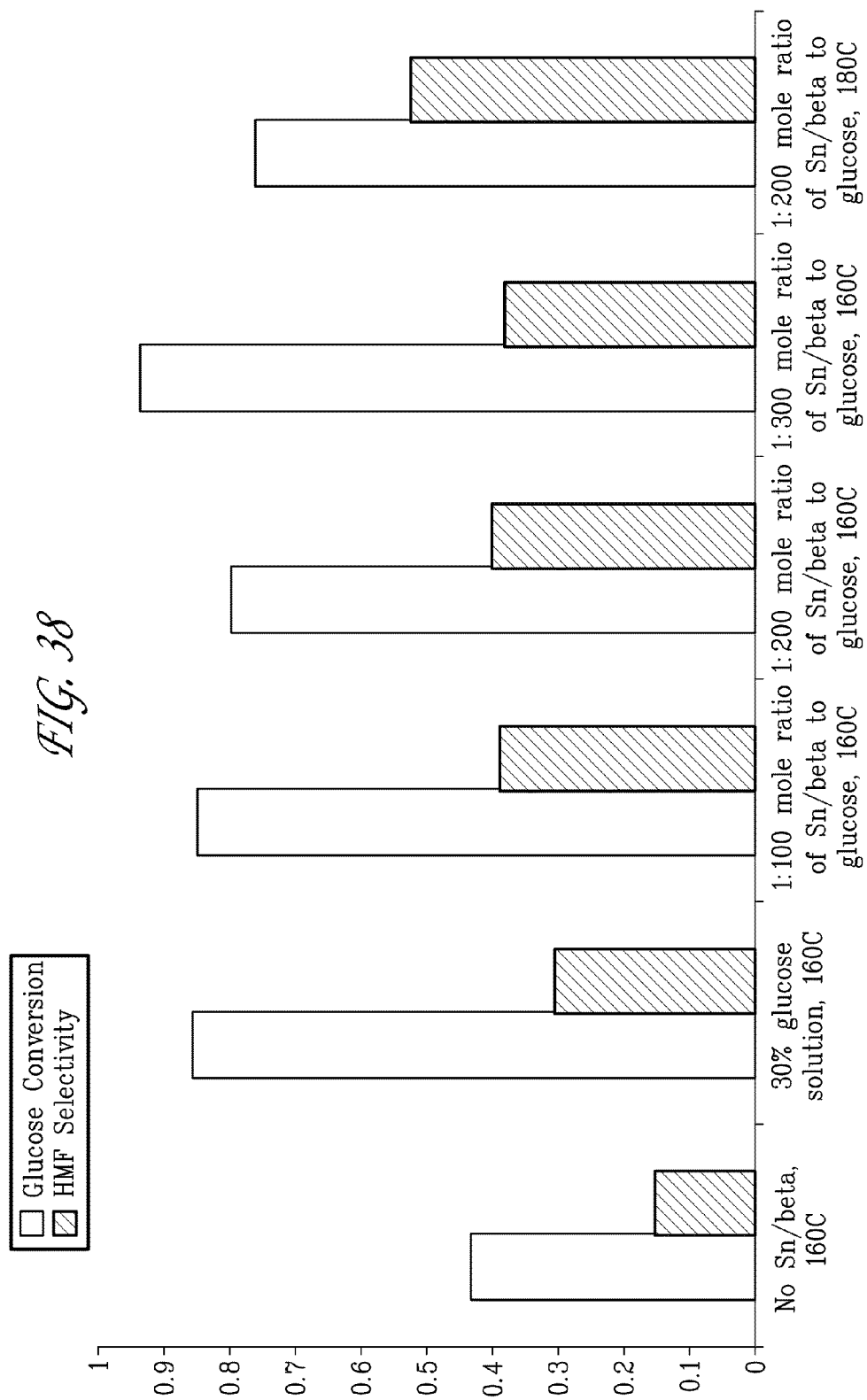
FIGS. 38-39 depict the results of reaction tests for the conversion of glucose to HMF using a biphasic system. The reaction conditions of the FIG. 38 series of experiments were 1:2 water to 1-butanol volume ratio, pH of 1 in HCl, and 35 g of NaCl in 100 g of water. The reaction conditions of the FIG. 39 series of experiments were 1:3 water to organic phase volume ratio, pH of 1 in HCl, T=180° C., 35 g of NaCl in 100 g of water.
Figure 39:
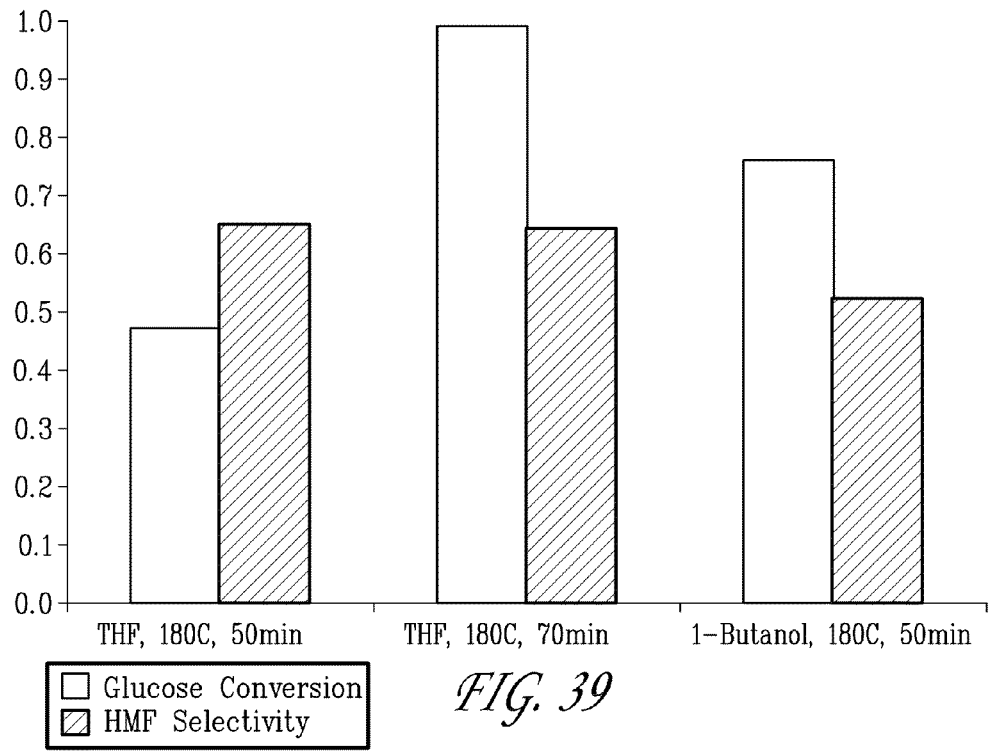
Figure 40:
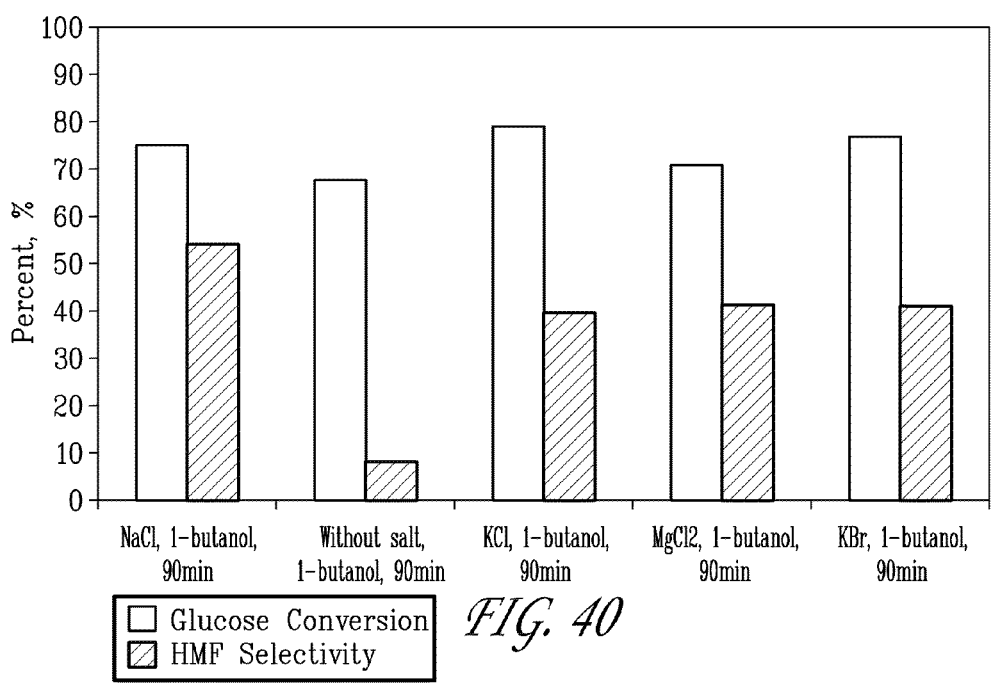
FIG. 40 depicts the results of reaction tests for the conversion of glucose to HMF using a biphasic system. The reaction conditions were Sn-Beta to glucose molar ratio of 200, 1:3 water to 1-butanol volume ratio, pH=1 in HCl, T=160° C., 35 g of salt in 100 g of water.
Figure 41:
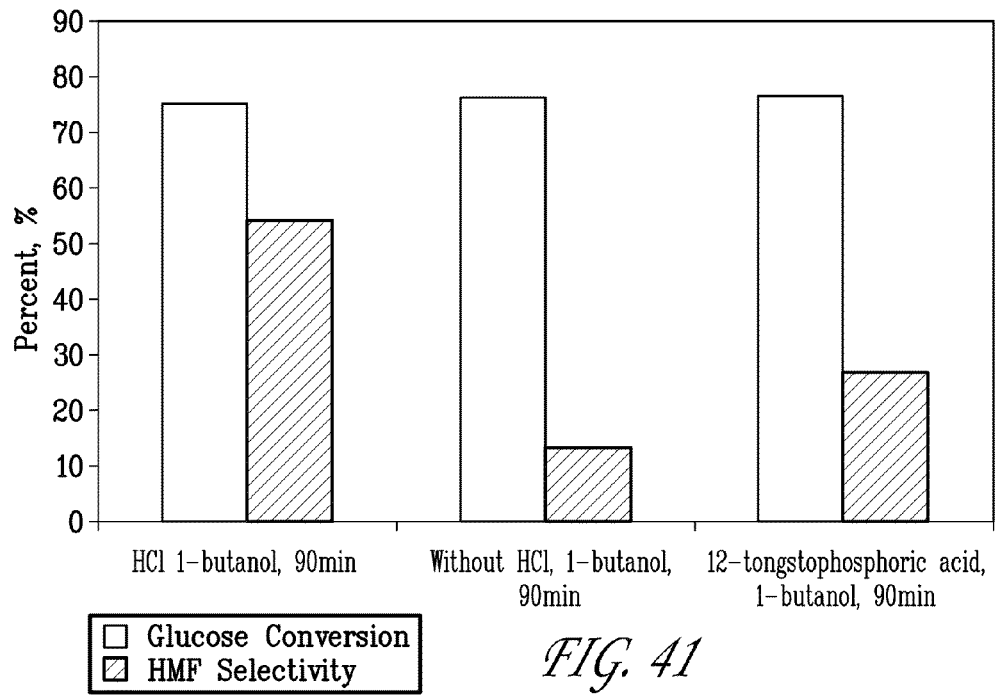
FIG. 41 depicts the results of reaction tests for the conversion of glucose to HMF using a biphasic system. The reaction conditions were Sn-Beta to glucose molar ratio of 200, 1:3 water to 1-butanol phase volume ratio, pH=1 in acid, T=160° C., 35 g of NaCl in 100 g of water.
Figure 42:
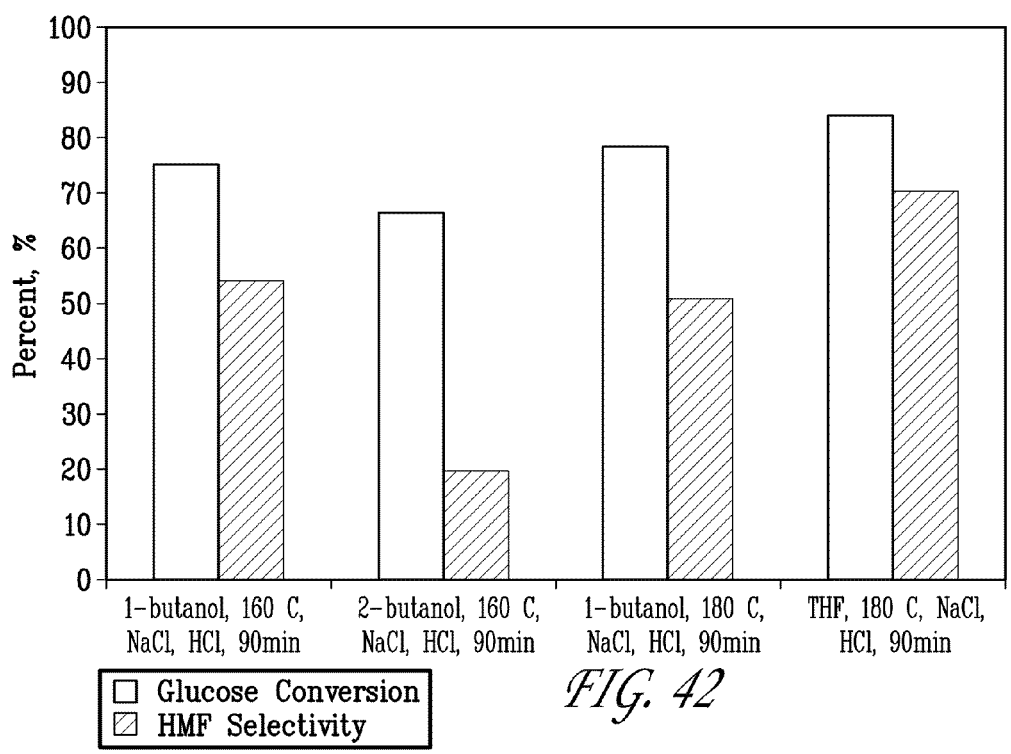
FIG. 42 depicts the results of reaction tests for the conversion of glucose to HMF using a biphasic system. The reaction conditions were Sn-Beta to glucose molar ratio of 200, 1:3 water to organic phase volume ratio, pH of 1 in HCl, 35 g of NaCl in 100 g of water.
Figure 43:
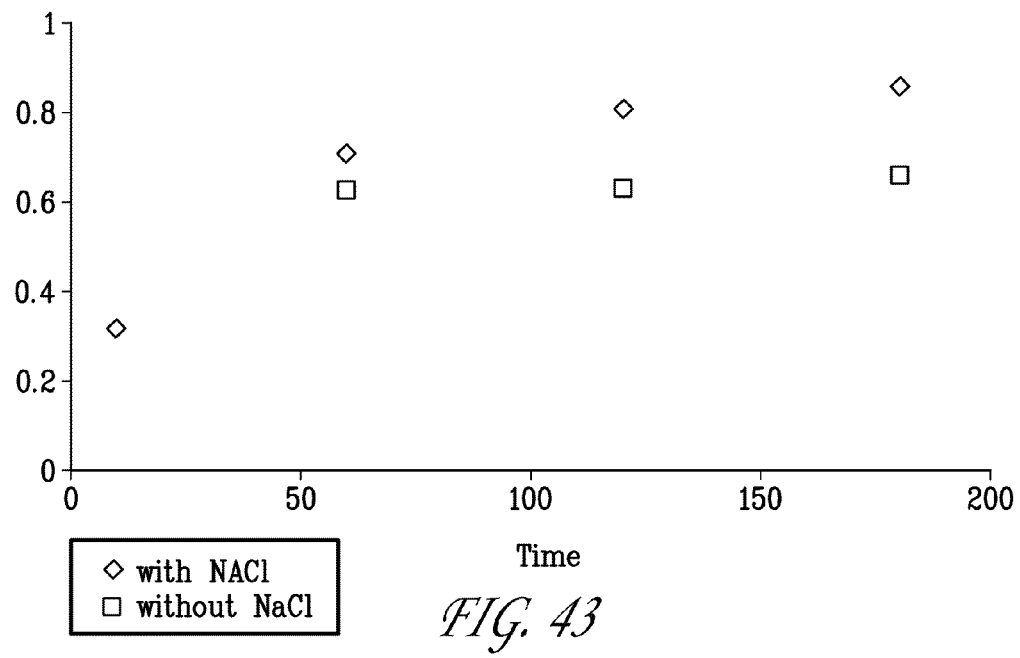
FIGS. 43-45 depict the results of reaction tests for the conversion of glucose to HMF using a biphasic system. The reaction conditions were temp 160° C., Sn/Beta zeolite to glucose mole ratio of 1:200, pH of 1 in HCl, 1:2 water to 1-butanol volume ratio.
Figure 44:
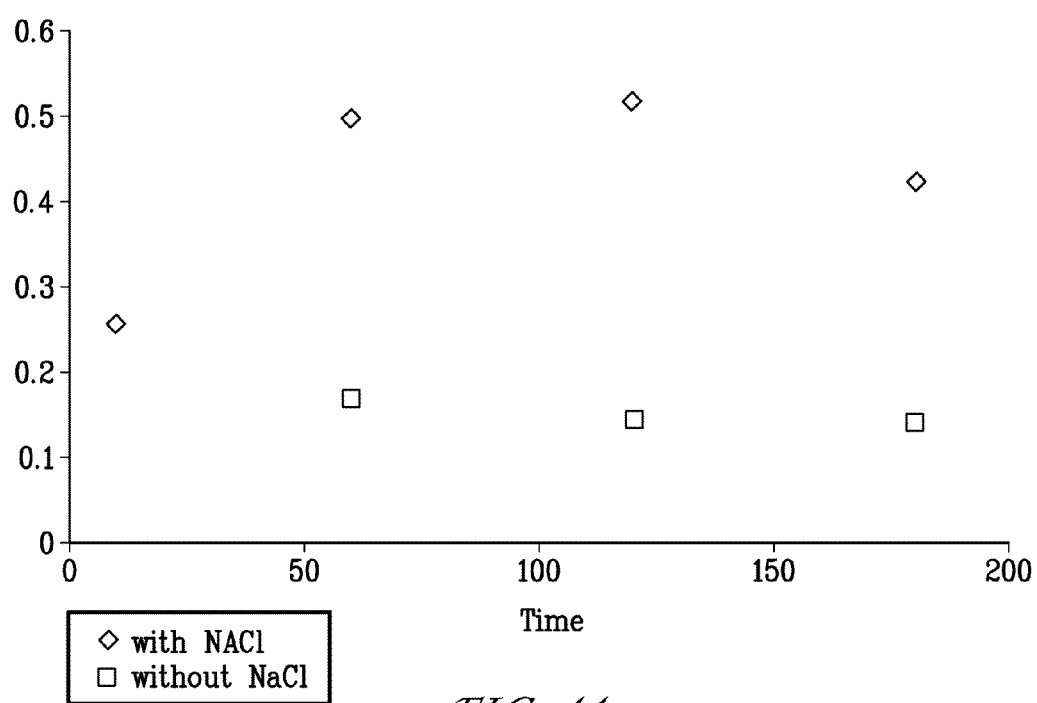
Figure 45:
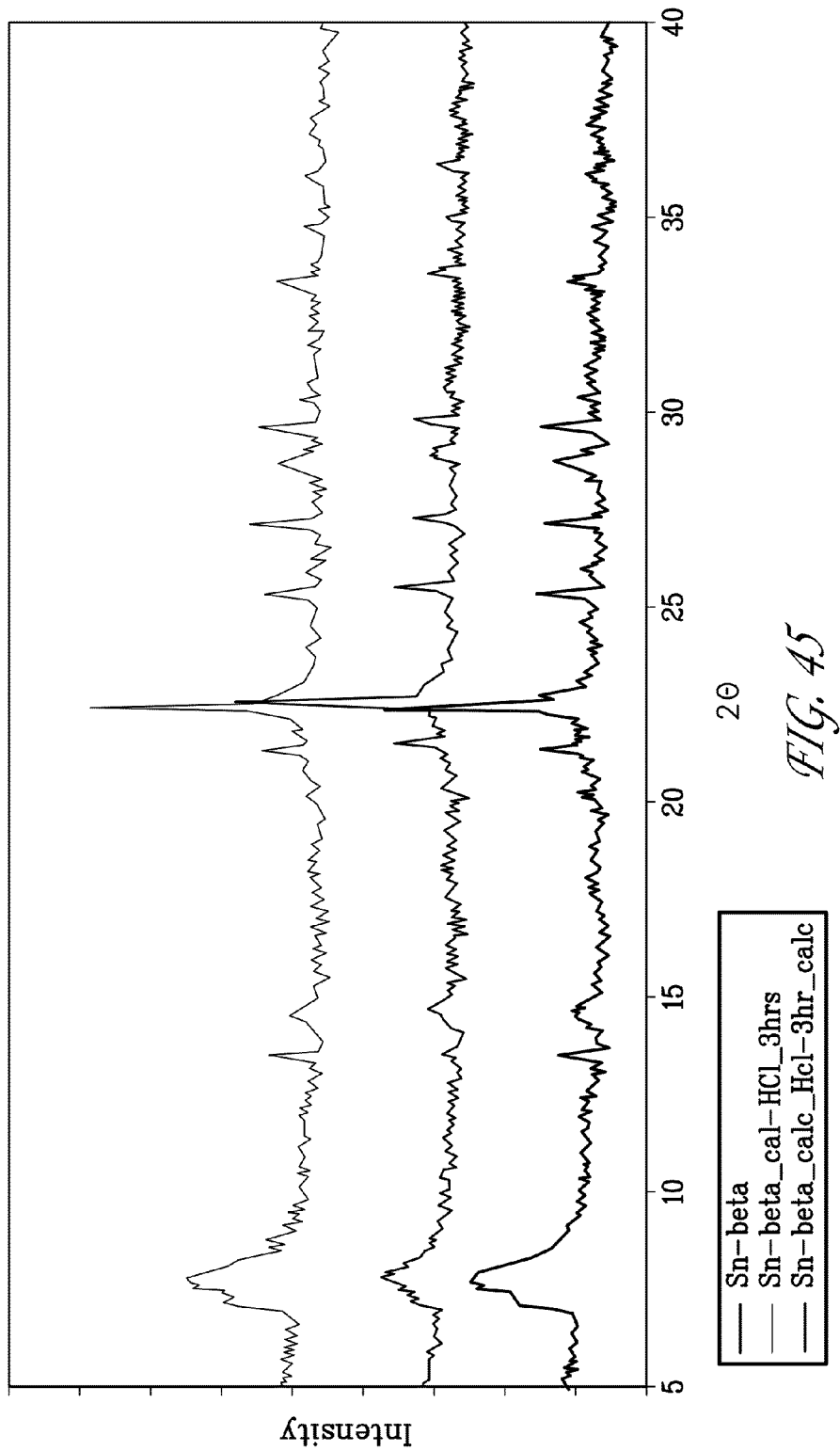

Glucose deuterated at the C-2 position (glucose-D2, FIG. 35) was used to perform NMR studies on the isomerization reaction. As shown in FIG. 18, the proton at the C-2 position plays a fundamental role in the reaction mechanism regardless of which pathway is followed. Indeed, isotopic substitution at the C-2 position resulted in a two-fold decrease in the initial reaction rate ($k_H/k_D$=1.98, FIG. 34), revealing a considerable kinetic isotopic effect. Importantly, $^{13}$C NMR spectra of glucose-D2 heated in water at the reaction temperature (383K) in the absence of catalyst reveal that no isotopic scrambling occurs (FIGS. 36-37). This result is important because it demonstrates the inertness of the C-D bond in water at reaction conditions and indicates that any isotopic rearrangement within the molecule during the reaction is entirely due to the actions of the catalyst.

Figure 31:
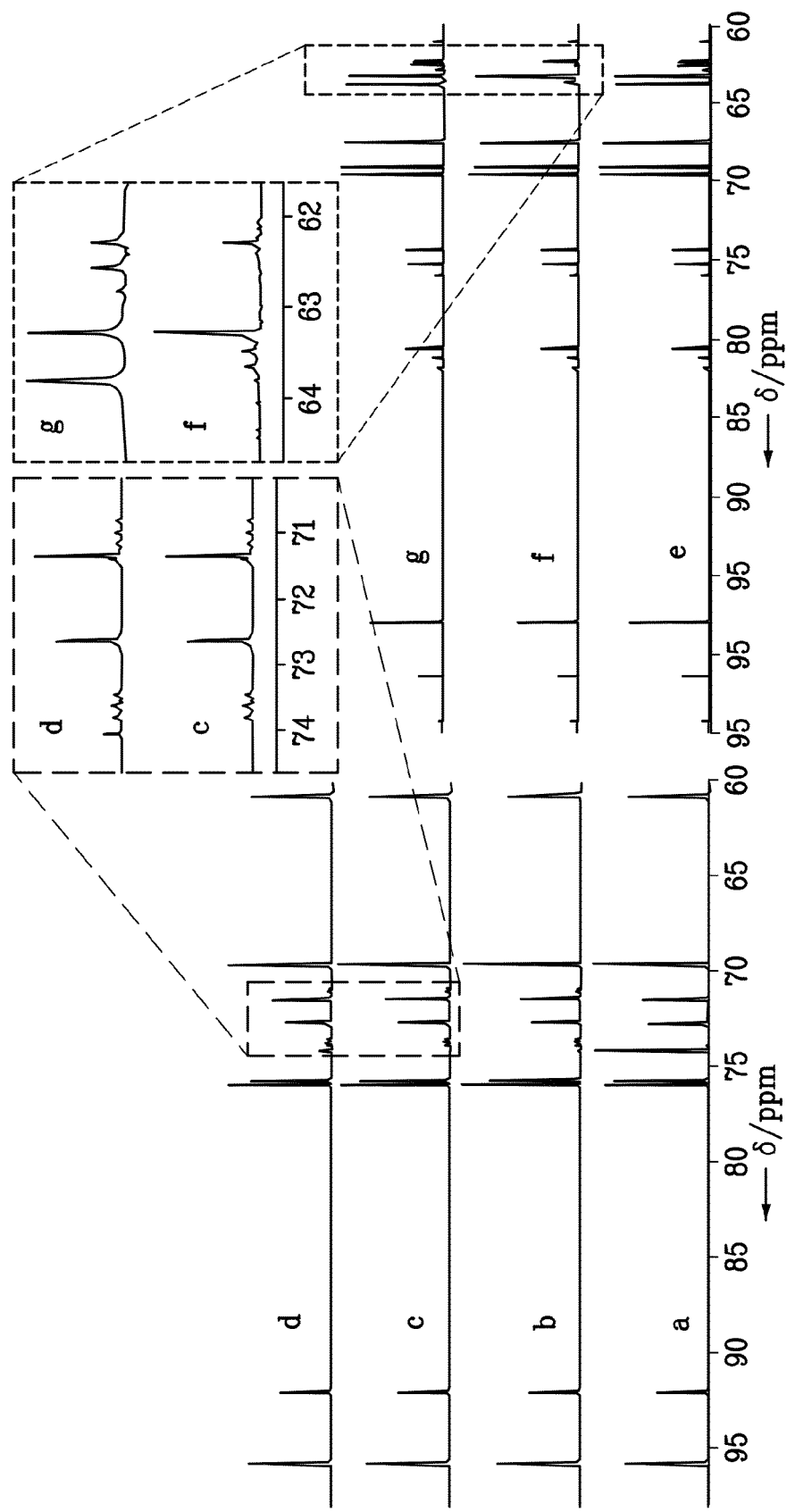
FIG. 31 depicts $^{13}$C NMR spectra of a) unlabeled glucose, b) labeled glucose-D2, c) glucose fraction obtained after reacting glucose-D2 with Sn-Beta, d) glucose fraction obtained after reacting labeled glucose-D2 with NaOH, e) unlabeled fructose, 0 fructose fraction obtained after reacting labeled glucose-D2 with Sn-Beta, and g) fructose fraction obtained after reacting labeled glucose-D2 with NaOH.

$^{13}$C and $^1$H NMR spectroscopy were used to study the isomerization of glucose-D2 using Sn-Beta as the catalyst. A comparison of $^{13}$C NMR spectra of unlabeled glucose and glucose-D2 feed solutions reveals that resonances observed at δ=74.1 and 71.3 ppm in the unlabeled glucose solution appear as low-intensity 1:1:1 triplets in the glucose-D2 solution (FIG. 31 a,b). This effect is related to the disruption of the nuclear Overhauser enhancement (NOE) by the deuterium atoms in the C-2 positions of the two configurations of glucose-D2 in solution (β-pyranose and α-pyranose, present in a 64:36 ratio). During NOE, $^{13}$C resonance intensities are enhanced up to 200% for directly bonded $^{13}$C—$^{1}$H pairs when $^{1}$H broad-band decoupling is used to suppress C,H couplings; however, this resonance amplification is not observed for $^{13}$C—$^{1}$H pairs and resonances associated with C-2 in glucose-D2 are thus substantially diminished. After reacting a 10 wt % solution of glucose-D2 in water at 383 K for 15 min in the presence of Sn-Beta, the glucose and fructose fractions were separated using high performance liquid chromatography (HPLC). Analysis of $^{13}$CNMR spectrum for each fraction shows that after reaction, glucose-D2 remains unchanged (FIG. 31 b,c), while the fructose product has significant differences compared to an unlabeled fructose standard (FIG. 31 e,f). Specifically, resonances at δ=63.8 and 62.6 ppm assigned to the C-1 position of the β-pyranose and β-furanose configurations in the unlabeled fructose standard appear as low-intensity triplets for the fructose product recovered after reaction. $^{1}$H NMR spectra for both sugars further confirm these results. The $^{1}$H NMR spectra of glucose-D2 before and after reaction remain constant (FIG. 32 b,c), while the fructose spectrum shows the disappearance of the resonance at δ=3.45 ppm due to the presence of a deuterium atom in the C-1 position (FIG. 32 f). Integration of the areas in these spectra confirms the presence of six C—H pairs for the glucose and fructose fractions in contrast to the seven C—H pairs found in unlabeled glucose or fructose. These results clearly indicate that the deuterium atom located in the C-2 position of glucose-D2 has moved to the C-1 position of fructose, thereby unequivocally demonstrating that the glucose isomerization reaction with a solid Lewis acid catalyst in pure water proceeds by means of an intramolecular hydride shift.

A similar spectroscopic study was performed using sodium hydroxide (NaOH) as a basic catalyst. A 10 wt % aqueous solution of glucose-D2 was reacted in the presence of NaOH (0.1M) at 383 K for 2 min. $^{13}$CNMR and $^{1}$HNMR spectra of the glucose and fructose fractions show considerable differences when compared to the results obtained with Sn-Beta. First, the $^{13}$C and $^{1}$HNMR spectra for the unlabeled fructose and for the fructose fraction isolated after reaction show no differences, indicating that the fructose fraction does not contain deuterium atoms (FIG. 31 e,g and FIG. 32 e,g). Second, the $^{13}$C NMR spectrum of the glucose fraction shows glucose-D2 mixed with a small amount of regular glucose, as indicated by the presence of a small resonance at δ=74.1 ppm (see inset in FIG. 31 d). The presence of unlabeled glucose is corroborated by the appearance of a resonance at δ=3.1 ppm in the $^{1}$H NMR spectrum, which is assigned to a proton in the C-2 position (FIG. 32 d). These results clearly indicate that the basic catalyst operates by a proton-transfer mechanism whereby the deuterium atom is removed from the a-carbonyl carbon of glucose-D2 to form the corresponding enolate, and a proton from solution is subsequently re-incorporated into the molecule, yielding some unlabeled glucose along with the unlabeled fructose (FIG. 18 A).

Figure 33A:
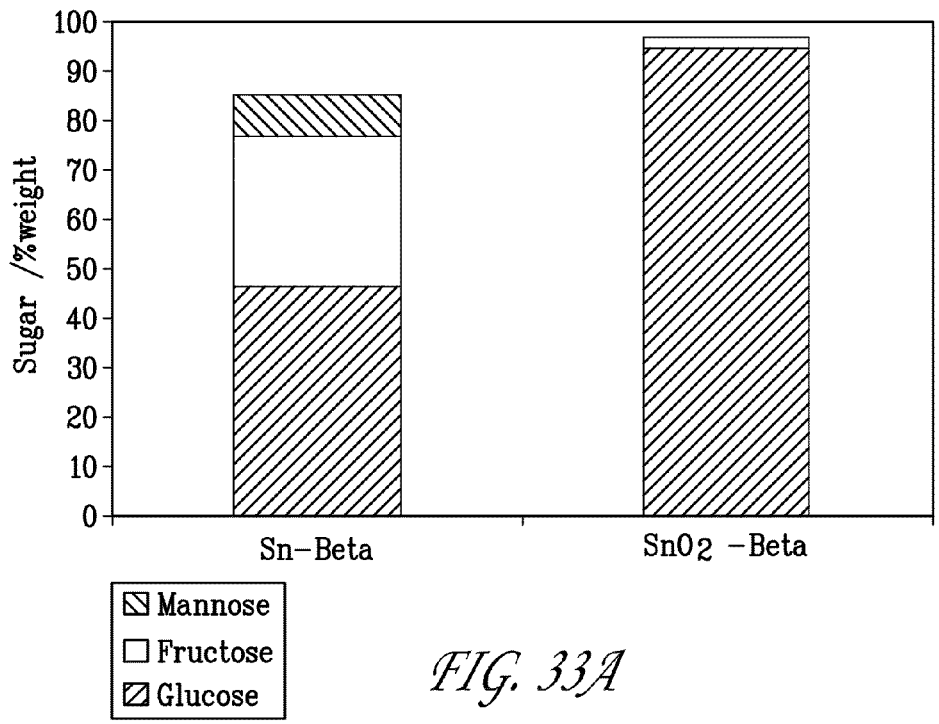
FIG. 33 depicts (A) Glucose isomerization reaction and product distributions (glucose-stripes from lower left to upper right, fructose-white, and stripes from upper right to lower left) after 45 minutes at 383 K using Sn-Beta or SnO$_2$-Beta. Reactions were performed with a 10 wt % glucose solution, using the corresponding amount of catalyst to maintain a 1:100 metal:glucose molar ratio; and (B) Diffuse reflectance UV-Vis spectra for Sn-Beta and SnO$_2$-Beta.
Figure 33B:
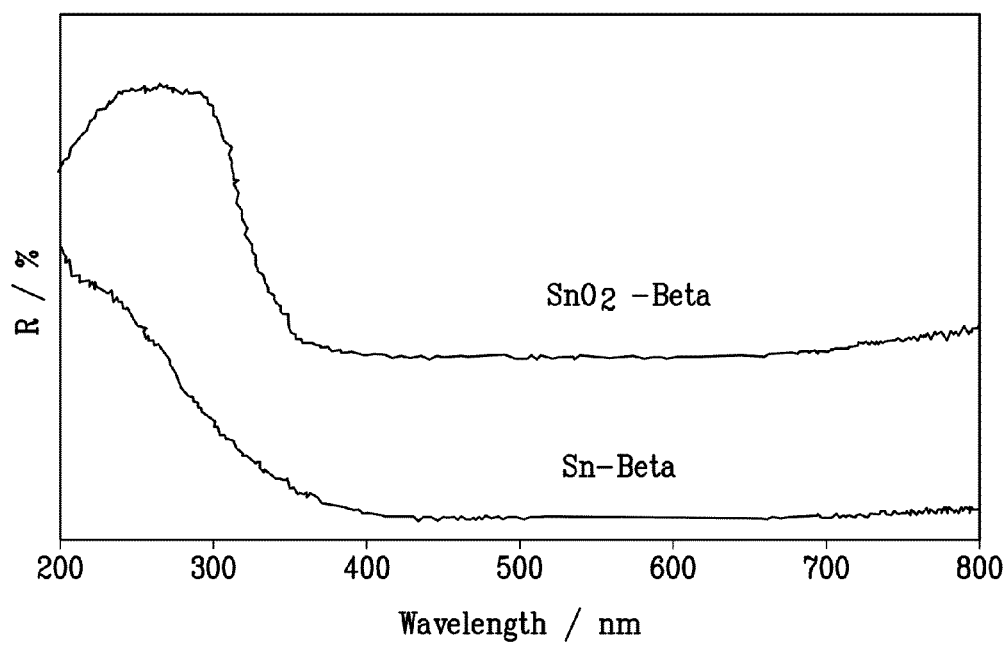

This experiment indicates that Sn-Beta can act as a Lewis acid capable of catalyzing the isomerization of glucose in a pure aqueous medium. Further studies are necessary in order to understand the nature of the interactions amongst the active site in Sn-Beta, the sugar and the solvent during the isomerization reaction. Previous reports by Corma and co-workers have shown (using $^{119}$Sn-NMR) that isolated framework tin centers in zeolites are responsible for drastically enhancing the rates of certain reactions. A. Corma, Nature 2001, 412, 423. For glucose isomerization in water, we observed that framework tin centers are necessary for Sn-Beta to catalyze the reaction. Sn-Beta synthesized by a procedure known to fully incorporate tin into the framework (SnCl, as the tin source) is highly active for the isomerization reaction, whereas Sn-Beta synthesized using SnO, as the tin source is completely inactive (FIG. 33A). The diffuse reflectance UV-Vis spectrum for the active material shows a single band centered at 220 nm, assigned to tetrahedrally coordinated metal, while the spectrum for the non-active material shows a band centered at 300 nm, assigned to octahedrally coordinated metal in extra-framework positions (FIG. 33B).

Example 13

The results of further glucose isomerization experiments are summarized in the following table:

| Entry | Solvent | Catalyst | Temp °C. | Time (min) | Glucose | Fructose | Mannose | Conversion % |
|---|---|---|---|---|---|---|---|---|
| 1 | H$_2$O | Sn-Beta | 110 | 90 | 35 | 30 | 13 | 65 |
| 2 | DMSO | Sn-Beta | 110 | 90 | 95 | 3 | 2 | 5 |
| 3 | DMSO/H$_2$O (8:2) | Sn-Beta | 110 | 90 | 93 | 2 | 1 | 7 |
| 4 | DMSO/H$_2$O (2:8) | Sn-Beta | 110 | 90 | 91 | 4 | 0 | 9 |
| 5 | DMSO (after water activation) | Sn-Beta | 110 | 90 | 96 | 1 | 0 | 4 |
| 6 | DMF | Sn-Beta | 110 | 90 | 89 | 5 | 4 | 11 |
| 7 | MeOH | Sn-Beta | 110 | 90 | 80 | 3 | 2 | 20 |

Example 14

The results of glucose to HMF conversion experiments are summarized in the following table:

| Entry | System | Catalyst | Temp °C. | Time (min) | Glucose Conversion % | HMF Selectivity % |
|---|---|---|---|---|---|---|
| 1 | Single phase in H$_2$O | Sn-Beta, HCl | 160 | 90 | 65 | 6 |
| 2 | Biphasic: H$_2$O/1-butanol | Sn-Beta, HCl | 160 | 90 | 5 | 25 |
| 3 | Biphasic: H$_2$O/1-butanol/NaCl | Sn-Beta, HCl | 160 | 90 | 7 | 53 |
| 4 | Biphasic: H$_2$O/1-butanol/NaCl | Sn-Beta | 160 | 90 | 9 | 16 |

-continued

| Entry | System | Catalyst | Temp °C. | Time (min) | Glucose Conversion % | HMF Selectivity % |
|---|---|---|---|---|---|---|
| 5 | Biphasic: H$_2$O/1-butanol/NaCl | Sn-Beta, HCl | 180 | 70 | 4 | 51 |
| 6 | Biphasic: H$_2$O/THF | Sn-Beta, HCl | 180 | 70 | 84 | 70 |

Example 15

Figure 47:
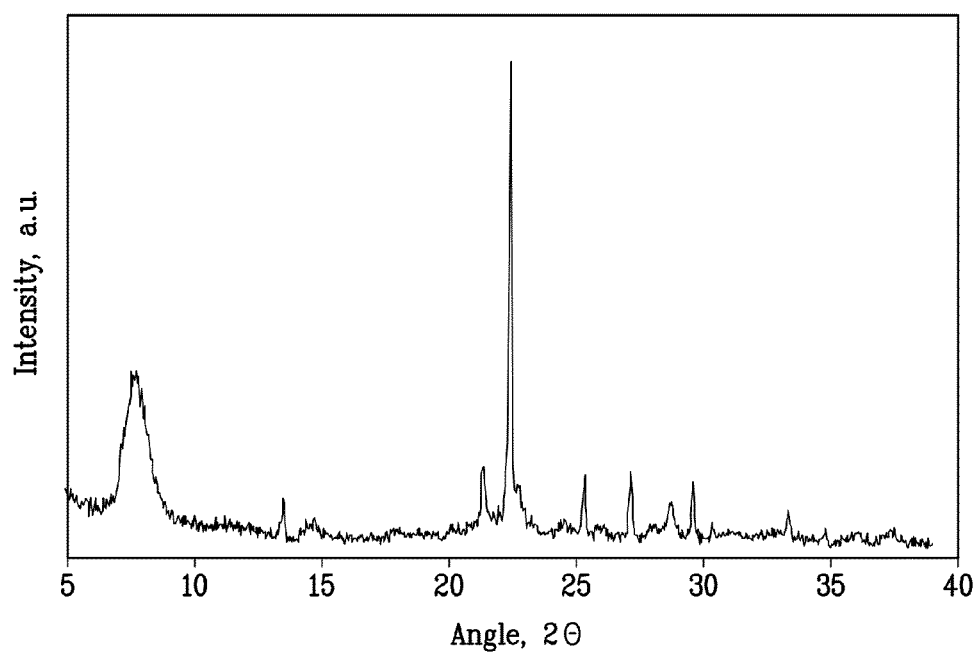
FIG. 47 depicts an x-ray defraction pattern of Zn-CIT-6 synthesized according to the procedure described in Andy & Davis, Ind. Eng. Chem. Res. 2004, 43, 2922.
Figure 48:
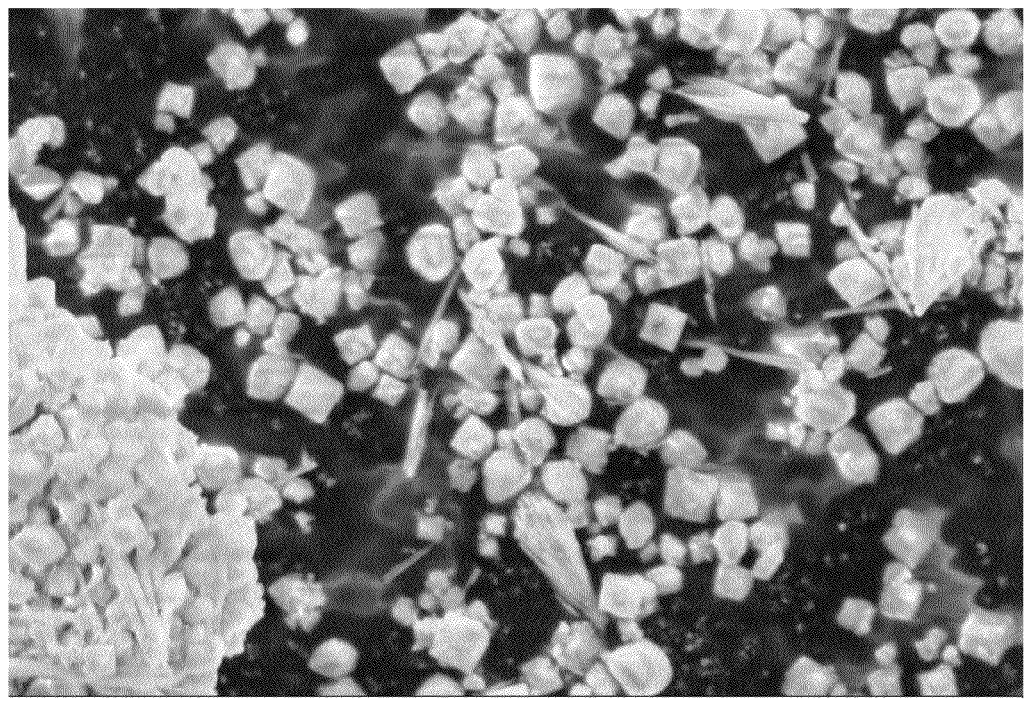
FIG. 48 depicts a scanning electronic micrograph of the synthesized Zn-CIT-6, showing a crystal size of 0.5-0.6 microns.

Zeolite Sn-CIT-6 was synthesized for the glucose isomerization reaction. The synthesis of the zincosilicate CIT-6 was done following the procedure described in the literature (Andy & Davis, Ind. Eng. Chem. Res. 2004, 43, 2922). The x-ray diffraction pattern of the as-synthesized material is depicted in FIG. 47. An electron micrograph of the as-synthesized material is depicted in FIG. 48. To eliminate the Zn from the framework, 1.0 g of zeolite was introduced in 60 mL of glacial acetic acid, and 100 mL of water, maintaining the mixture at 80° C. during 3 days. CIT-6 was recovered by filtration washing the solid with water, and dried overnight at 100° C. Next, the sample was heated to 130° C. for 2 h with vacuum to eliminate the adsorbed water. The grafting of Sn (in the form of SnCl$_3$CH$_3$) in the CIT-6 was carried out with a solution of the corresponding amount of grafting agent (Si/Sn ~100-125) in anhydrous chloroform at room temperature. After 1 h, triethylamine was added in the mixture to trap the hydrochloric acid formed in the grafting process. The suspension was maintained stirred during 2 days. The sample was washed with chloroform and dried at 100° C. overnight. The final ratio of Si/Sn was 110 for CIT-6(SnCH$_3$Cl$_3$) (calculated by EDS). A portion amount of the sample was calcined at 580° C. for 6 hours.

Figure 49:
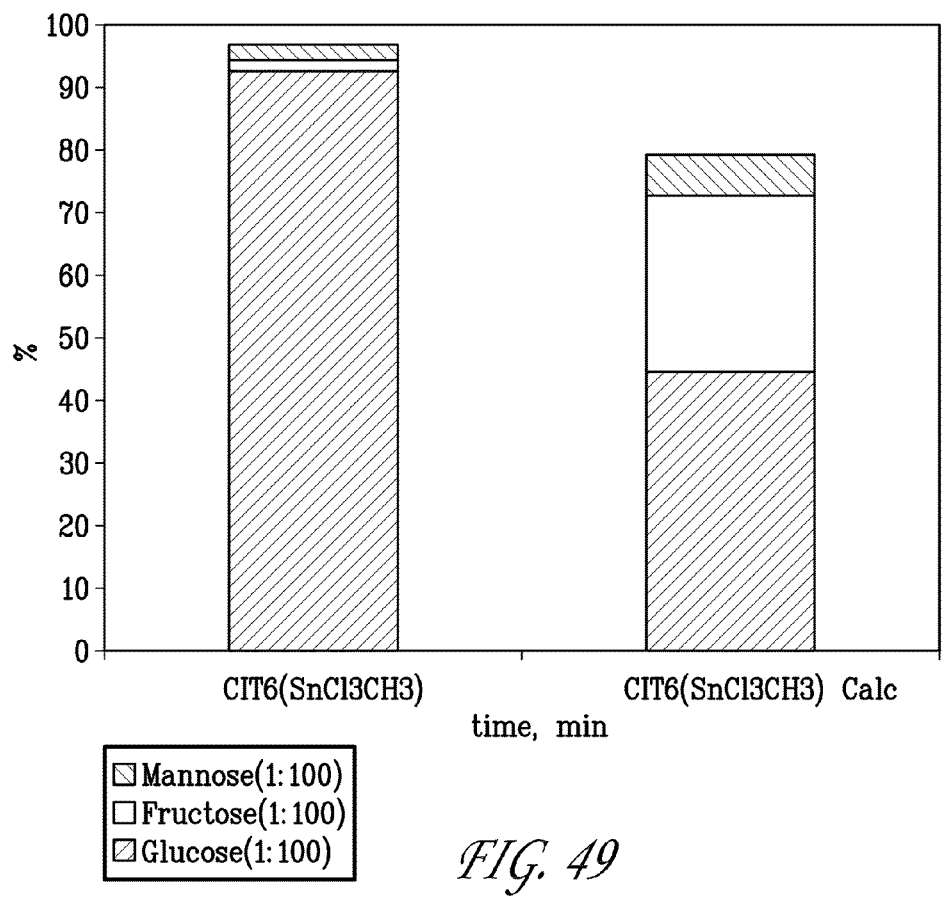
FIG. 49 depicts product distributions for the glucose isomerization reaction at 110° C. by using the CIT-6 (SnCH$_3$Cl$_3$) catalyst in the as prepared form (left) and calcined (right)

The reaction conditions for the glucose isomerization were: 10% wt of glucose in water with a sugar:Sn ratio of 100 at 110° C. after 90 minutes. As shown in FIG. 49, when CIT-6(SnCH$_3$Cl$_3$) was calcined, the catalyst was active for the glucose isomerization reaction. This suggests that for an effective grafting, the alkyl groups should be removed oxidatively by calcination. This trend was also observed and described by Corma et al., J. Catal, 2003, 219, 242. FIG. 49 depicts product distributions for the glucose isomerization reaction at 110° C. by using the CIT-6(SnCH$_3$Cl$_3$) catalyst in the as prepared form (left) and calcined (right).

What is claimed:

1. A process comprising (a) isomerizing a monosaccharide comprising contacting the monosaccharide in aqueous medium with a high-silica zeolite containing tetrahedrally coordinated tin or titanium incorporated into the framework of the zeolite, the zeolite having pores capable of admitting the monosaccharide, and (b) recovering an isomerized monosaccharide.

2. The process of claim 1, wherein the zeolite has a *BEA topology.

3. The process of claim 2, wherein the monosaccharide is a pentose or hexose.

4. The process of claim 2, wherein the monosaccharide is glucose, fructose, or mannose.

5. The process of claim 1, wherein the aqueous medium comprises between about 10 weight percent monosaccharide and about 50 weight percent monosaccharide.

6. The process of claim 1, wherein the isomerization substantially reaches thermodynamic equilibrium.

7. The process of claim 2, wherein the aqueous medium is acidic.

8. The process of claim 1, wherein the aqueous medium has a pH in a range of from about 0 to about 2.

9. The process of claim 1, wherein the aqueous medium comprises a salt.

10. The process of claim 9, wherein the salt comprises acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, or bis-trifluorsulfonimide.

11. The process of claim 9, wherein the salt is sodium chloride, potassium chloride, magnesium chloride, or potassium bromide.

12. The process of claim 1, wherein the isomerization is carried out at a temperature of between about 90° C. and about 180° C.

13. The process of claim 1, wherein the isomerization is carried out for less than about 90 minutes.

14. The process of claim 1, wherein the zeolite is used batchwise for at least three reaction cycles without significant reduction in performance and without the need for calcination.

15. A process comprising (a) isomerizing a monosaccharide comprising contacting the monosaccharide in aqueous medium with an ordered mesoporous silica material containing tin or titanium incorporated into the framework of the material, and (b) recovering an isomerized monosaccharide.

16. The process of claim 15, wherein the ordered mesoporous silica material is MCM-41.

17. A process for converting glucose to 5-hydroxymethylfurfural comprising:
 contacting glucose in aqueous medium with a high silica zeolite containing tin or titanium incorporated into the framework of the zeolite, the zeolite having pores capable of admitting the glucose, to provide fructose; and
 dehydrating the fructose.

18. The process of claim 17, further comprising maintaining the fructose in the aqueous medium while it is dehydrated.

19. The process of claim 17, wherein the dehydration is carried out in the presence of an acid catalyst.

20. The process of claim 19, wherein the catalyst is an inorganic acid dissolved in the aqueous medium.

21. The process of claim 19, wherein the catalyst is a solid acid catalyst.

22. The process of claim 19, wherein the catalyst is protonated high silica zeolite having a *BEA topology.

23. The process of claim 17, wherein the aqueous medium has a pH in a range of from about 0 to about 2.

24. The process of claim 17, wherein the aqueous medium comprises a salt.

25. The process of claim 24, wherein the salt comprises acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, or bis-trifluorsulfonimide.

26. The process of claim 24, wherein the salt is sodium chloride, potassium chloride, magnesium chloride, or potassium bromide.

27. The process of claim 17, wherein the zeolite has a *BEA topology.

28. The process of claim 17, wherein the aqueous medium comprises between about 10 weight percent glucose and about 50 weight percent glucose.

29. The process of claim 18, wherein the aqueous medium is contacted with an organic medium capable of extracting 5-hydroxymethylfurfural from the aqueous medium, wherein the organic medium is substantially immiscible with the aqueous medium.

30. The process of claim 29, wherein 5-hydroxymethylfurfural is produced in the aqueous medium, and extracted from the aqueous medium to the organic medium as it is produced.

31. The process of claim 29, wherein the organic medium comprises a solvent, wherein the solvent is a water-immiscible, linear, branched, or cyclic alcohol, ether, or ketone.

32. The process of claim 29, wherein the organic medium comprises a solvent, wherein the solvent is an unsubstituted aliphatic or aromatic hydrocarbon, or a halo-substituted aliphatic or aromatic hydrocarbon.

33. The process of claim 29, wherein the organic medium comprises 1-butanol or THF.

34. A process for converting starch to 5-hydroxymethylfurfural comprising:
hydrolyzing the starch in acid to provide glucose in an acidic aqueous medium;
contacting glucose in aqueous medium with a high silica zeolite containing tin or titanium incorporated into the framework of the zeolite, the zeolite having pores capable of admitting the glucose, to provide fructose; and
dehydrating the fructose.

35. The process of claim 34, further comprising maintaining the glucose in the acidic aqueous medium while it is contacted with high silica zeolite to provide fructose.

36. The process of claim 35, further comprising maintaining the fructose in the acidic aqueous medium while it is dehydrated to provide 5-hydroxymethylfurfural.

37. The process of claim 36, wherein the acidic aqueous medium is contacted with an organic medium capable of extracting 5-hydroxymethylfurfural from the acidic aqueous medium, wherein the organic medium is substantially immiscible with the aqueous medium.

38. The process of claim 37, wherein 5-hydroxymethylfurfural is produced in the acidic aqueous medium, and extracted from the aqueous medium to the organic medium as it is produced.

39. A process comprising (a) isomerizing a monosaccharide comprising contacting the monosaccharide in aqueous medium with a high-silica zeolite containing tin or titanium incorporated into the framework of the zeolite, the zeolite having pores capable of admitting the monosaccharide, wherein the tin or titanium acts as a Lewis acid, and (b) recovering an isomerized monosaccharide.

40. The process of claim 39, wherein the zeolite has a *BEA topology.

41. The process of claim 39, wherein the aqueous medium comprises between about 10 weight percent monosaccharide and about 50 weight percent monosaccharide.

42. The process of claim 39, wherein aqueous medium is acidic.

43. The process of claim 39, wherein the aqueous medium comprises a salt.

44. A process comprising (a) isomerizing a disaccharide comprising contacting the disaccharide in aqueous medium with a high-silica zeolite containing tetrahedrally coordinated tin or titanium incorporated into the framework of the zeolite, the zeolite having pores capable of admitting the disaccharide, and (b) recovering an isomerized disaccharide.

45. The process of claim 44, wherein the zeolite has a *BEA topology.

46. The process of claim 44, wherein the disaccharide is lactose.

47. The process of claim 44, wherein the aqueous medium comprises between about 10 weight percent disaccharide and about 50 weight percent disaccharide.

48. The process of claim 44, wherein the aqueous medium has a pH in a range of from about 0 to about 2.

49. The process of claim 44, wherein the aqueous medium comprises sodium chloride, potassium chloride, magnesium chloride, or potassium bromide.

50. A process comprising (a) isomerizing a disaccharide comprising contacting the disaccharide in aqueous medium with an ordered mesoporous silica material containing tin or titanium incorporated into the framework of the material, and (b) recovering an isomerized disaccharide.

51. The process of claim 50, wherein the ordered mesoporous silica material is MCM-41.

52. The process of claim 50, wherein the disaccharide is lactose.

53. The process of claim 50, wherein the aqueous medium comprises between about 10 weight percent disaccharide and about 50 weight percent disaccharide.

54. The process of claim 50, wherein the aqueous medium has a pH in a range of from about 0 to about 2.

55. The process of claim 50, wherein the aqueous medium comprises sodium chloride, potassium chloride, magnesium chloride, or potassium bromide.

56. A process comprising (a) isomerizing a disaccharide comprising contacting the disaccharide in aqueous medium with a high-silica zeolite containing tin or titanium incorporated into the framework of the zeolite, the zeolite having pores capable of admitting the disaccharide, wherein the tin or titanium acts as a Lewis acid, and (b) recovering an isomerized disaccharide.

57. The process of claim 56, wherein the zeolite has a *BEA topology.

58. The process of claim 56, wherein the disaccharide is lactose.

59. The process of claim 56, wherein the aqueous medium comprises between about 10 weight percent disaccharide and about 50 weight percent disaccharide.

60. The process of claim 56, wherein the aqueous medium is acidic.

61. The process of claim 56, wherein the aqueous medium comprises sodium chloride, potassium chloride, magnesium chloride, or potassium bromide.

62. A process for isomerizing a monosaccharide comprising contacting the monosaccharide in aqueous medium with a high-silica zeolite containing tetrahedrally coordinated tin or titanium incorporated into the framework of the zeolite, the zeolite having pores capable of admitting the monosaccharide, wherein:
(a) the aqueous medium has a pH in a range of from about 0 to about 2; or
(b) the aqueous medium comprises a salt; or
(c) both (a) and (b).

63. The process of claim 62, wherein the zeolite has a *BEA topology.

64. The process of claim 62, wherein the monosaccharide is glucose.

65. The process of claim 62, wherein the aqueous medium comprises between about 10 weight percent monosaccharide and about 50 weight percent monosaccharide.

66. The process of claim 62, wherein the salt comprises acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, or bis-trifluorsulfonimide.

67. The process of claim 66, wherein the salt is sodium chloride, potassium chloride, magnesium chloride, or potassium bromide.

68. The process of claim 62, wherein the isomerization is carried out at a temperature of between about 90° C. and about 180° C.

69. The process of claim 62, wherein the isomerization is carried out for less than about 90 minutes.

70. The process of claim 62, wherein the zeolite is used batchwise for at least three reaction cycles without significant reduction in performance and without the need for calcination.

\* \* \* \* \*